United States Patent
Tirinato et al.

(10) Patent No.: US 9,015,055 B2
(45) Date of Patent: Apr. 21, 2015

(54) MEDICAL DATA ACQUISITION AND PATIENT MANAGEMENT SYSTEM AND METHOD

(75) Inventors: Jody Ann Tirinato, Plainsboro, NJ (US); Mark Paul Maund, Lawrenceville, NJ (US); Paul Machiaverna, Spotswood, NJ (US); Paul Andrew Gibson, Metuchen, NJ (US); Gary John Vandersleen, Plainsboro, NJ (US); Rosa Margarita Ibanez, Bordentown, NJ (US); Lyudmila Zaltsman, Princeton, NJ (US); Michael P. Zelin, Plainsboro, NJ (US)

(73) Assignee: Abbott Point of Care Inc., Princeton, NJ (US)

( * ) Notice: Subject to any disclaimer, the term of this patent is extended or adjusted under 35 U.S.C. 154(b) by 720 days.

(21) Appl. No.: 11/777,700

(22) Filed: Jul. 13, 2007

(65) Prior Publication Data
US 2008/0065420 A1 Mar. 13, 2008

Related U.S. Application Data

(60) Provisional application No. 60/830,332, filed on Jul. 13, 2006.

(51) Int. Cl.
G06Q 50/22 (2012.01)
G06F 19/00 (2011.01)
G06Q 50/24 (2012.01)

(52) U.S. Cl.
CPC .......... *G06F 19/322* (2013.01); *G06F 19/3406* (2013.01); *G06F 19/363* (2013.01); *G06F 19/366* (2013.01); *G06Q 50/24* (2013.01)

(58) Field of Classification Search
CPC .................................................... G06Q 50/22
USPC ............................................................ 705/3
See application file for complete search history.

(56) References Cited

U.S. PATENT DOCUMENTS

| 4,933,048 A | 6/1990 | Lauks et al. |
| 4,954,087 A | 9/1990 | Lauks et al. |

(Continued)

FOREIGN PATENT DOCUMENTS

| JP | H05-146405 | 6/1993 |
| JP | H09-140748 | 6/1997 |

(Continued)

OTHER PUBLICATIONS

PCT International Search Report and the Written Opinion of the International Searching Authority regarding International Application No. PCT/US07/73526, as mailed on Sep. 12, 2008.

(Continued)

*Primary Examiner* — Michael Fuelling

(57) ABSTRACT

A sample analysis and medical data acquisition system for patient management includes a first user interface (UI) display module for displaying a medical chart page that includes selectable items associated with patient management. The first UI display module displays a set of medical delivery systems associated with a selectable medical delivery selection item, from which a medical delivery system is chosen. The system includes a second UI display module, in communication with the first UI display module, for displaying parameter fields for entry of operation data associated with the chosen medical delivery system. Medical data is captured from a patient by an analyzer configured to perform analysis of samples from the patient. The medical data is analyzed in accordance with entered operation data. The system includes an analysis display module, in communication with at least the first UI display module, for displaying sample analysis results.

26 Claims, 17 Drawing Sheets

(56) References Cited

U.S. PATENT DOCUMENTS

| | | | |
|---|---|---|---|
| 5,096,669 A | 3/1992 | Lauks et al. | |
| 5,112,455 A | 5/1992 | Cozzette et al. | |
| 5,124,661 A | 6/1992 | Zelin et al. | |
| 5,200,051 A | 4/1993 | Cozzette et al. | |
| 5,447,440 A | 9/1995 | Davis et al. | |
| 6,055,506 A * | 4/2000 | Frasca, Jr. | 705/3 |
| 6,379,883 B2 | 4/2002 | Davis et al. | |
| 6,438,498 B1 | 8/2002 | Opalsky et al. | |
| 7,077,328 B2 * | 7/2006 | Krishnaswamy et al. | 235/472.01 |
| 8,069,418 B2 * | 11/2011 | Monteleone | 715/781 |
| 2002/0060247 A1 | 5/2002 | Krishnaswamy et al. | |
| 2003/0208465 A1 * | 11/2003 | Yurko et al. | 707/1 |
| 2004/0024615 A1 * | 2/2004 | Monteleone et al. | 705/2 |
| 2004/0158193 A1 | 8/2004 | Bui et al. | |
| 2004/0172306 A1 * | 9/2004 | Wohl et al. | 705/3 |
| 2004/0173456 A1 | 9/2004 | Boos et al. | |
| 2004/0260204 A1 * | 12/2004 | Boecker et al. | 600/584 |
| 2005/0055244 A1 | 3/2005 | Mullan et al. | |
| 2005/0124866 A1 | 6/2005 | Elaz et al. | |
| 2006/0026205 A1 | 2/2006 | Butterfield | |
| 2006/0106649 A1 | 5/2006 | Eggers et al. | |
| 2006/0167381 A1 | 7/2006 | Azer et al. | |

FOREIGN PATENT DOCUMENTS

| | | |
|---|---|---|
| JP | H09-253056 | 9/1997 |
| JP | H10-079770 | 3/1998 |
| JP | 2002-282217 | 10/2002 |
| WO | WO 98/41271 A1 | 9/1998 |
| WO | 2006015330 A2 | 2/2006 |

OTHER PUBLICATIONS

European Search Report for EP 07 812 943.4 dated Oct. 24, 2011.
i-STAT, "Take Patient Care Anywhere," Mar. 11, 2006, XP002660968, pp. 1-4.
Donovan, P., "Procedure Manual for the i-Stat® System," Jul. 12, 2004, XP002660969, pp. 1-39.
Alpert, N., "I-STAT Point-of-Care Testing System," Clinical Instrument Systems, McNamara Pub., New York, NY, vol. 13, No. 4, 1, Jan. 1, 1994, XP002139627, pp. 1-7.
Office Action for corresponding Japanese Appl. No. 2012-273110 dated Oct. 16, 2013.
Japanese Office Action for JP2009-519714 dated Dec. 21, 2011.
Office Action for corresponding Japanese Appl. No. 2012-273110 dated Oct. 16, 2014.

* cited by examiner

Choices: Press MENU (205)
PtTemp      96.3°F (210)
CPB         Yes (215)
Sample Type VEN (220)
Site        L Brachial (225)
Allen's Test Pass
DelSys      ___ (230)

→ Page
Results Ready

FIG. 4B

DelSys (410)

0 - No Selection
1 - Room Air
2 - Nasal Air
3 - Bagging
4 - NonRb Mask
5 - VentiMask
6 - Adult Vent
7 - infant Vent
8 - SimpleMask
9 - AerosolMask (415)

← More →
Results Ready

Scan or Enter Data
IT    ____
RR    ____
Vt    ____
FIO2  ____

(425)

→ Page
Results Ready

Choices: Press MENU (205)
PtTemp      96.3° F (210)
CPB         Yes (215)
Sample Type VEN (220)
Site        L Brachial (225)
Allen's Test Pass
DelSys      VentiMask (230)

→ Page
Results Ready

MEDICAL DATA ACQUISITION AND PATIENT MANAGEMENT SYSTEM AND METHOD

The present application claims priority under 35 U.S.C. §119(e) to U.S. Provisional Application No. 60/830,332, filed on Jul. 13, 2006, the entire contents of which are hereby incorporated by reference herein.

BACKGROUND

1. Field of the Invention

The present invention relates to patient management systems. More particularly, the present invention relates to a system and method for sample analysis and medical data acquisition for patient management.

2. Background Information

Point-of-care sample analysis systems are generally based on a re-usable reading apparatus that performs sample tests using a disposable device, e.g., a cartridge or strip, that contains analytical elements, e.g., electrodes or optics for sensing analytes such as, for example, pH, oxygen and glucose. The disposable device can optionally include fluidic elements (e.g., conduits for receiving and delivering the sample to the electrodes or optics), calibrant elements (e.g., aqueous fluids for standardizing the electrodes with a known concentration of the analyte), and dyes with known extinction coefficients for standardizing optics. The reading apparatus contains the electrical circuitry and other components for operating the electrodes or optics, making measurements, and doing computations. The reading apparatus also has the ability to display results and communicate those results to laboratory and hospital information systems (LIS and HIS, respectively), for example, via a computer workstation. Communication between the reading apparatus and a workstation, and between the workstation and a LIS, can be via, for example, an infrared link, a wired connection, wireless communication, or any other form of data communication that is capable of transmitting and receiving (e.g., electrical) information, or any combination thereof.

One benefit of point-of-care sample testing systems is the elimination of the time-consuming need to send a sample to a central laboratory for testing. Point-of-care sample testing systems allow a nurse, at the bedside of a patient, to obtain a reliable, quantitative, analytical result, comparable in quality to that which would be obtained in a laboratory. In operation, the nurse selects a device with the required panel of tests, draws a sample, dispenses it into the device, optionally seals the device with, for example, a snap-closure, and inserts the device into the reading apparatus. While the particular order in which the steps occur may vary between different point-of-care systems and providers, the intent of providing rapid sample test results close to the location of the patient remains. The reading apparatus then performs a test cycle, i.e., all the other analytical steps required to perform the tests. Such simplicity gives the physician quicker insight into a patient's physiological status and, by reducing the time for diagnosis, enables a quicker decision by the physician on the appropriate treatment, thus enhancing the likelihood of a successful patient treatment.

In the emergency room and other acute-care locations within a hospital, the types of sample tests required for individual patients tend to vary. Thus, point-of-care systems generally offer a range of disposable devices with different sample tests, or combinations of sample tests. For example, for blood analysis devices, in addition to traditional blood tests, including oxygen ("PO2"), carbon dioxide ("PCO2"), pH, potassium ("K"), sodium ("Na"), chloride ("Cl"), hematocrit ("Hct"), glucose ("Glu"), urea ("BUN"), creatinine ("CREA") and calcium ("iCa"), other tests can include, for example, prothrombin time ("PT"), activated clotting time ("ACT"), activated partial thromboplastin time ("APTT"), troponin, creatine kinase MB ("CKMB") and lactate. While devices typically contain between one and ten tests, it will be appreciated by persons of ordinary skill in the art that any number of tests can be contained on a device. For example, a device for genetic screening can include numerous tests. To illustrate the need for different devices, a patient suspected of arrhythmia could require a device with a test combination that includes a potassium test, whereas a patient suspected of a diabetic coma can require a device with a test combination that includes a glucose test.

A given hospital may use numerous different types of devices and accordingly needs to maintain a combination of some or all of these at each point-of-care testing location within the hospital. These locations can include, for example, an emergency room (ER), a critical care unit (CCU), a pediatric intensive care unit (PICU), an intensive care unit (ICU), a renal dialysis unit (RDU), an operating room (OR), a cardiovascular operating room (CVOR), general wards (GW) and the like. Other hospital locations can be used to deliver point-of-care testing, as can other non-hospital-based locations where medical care is delivered, including, for example, MASH units, nursing homes, and cruise, commercial and military ships, and the like.

The following patents relating to point-of-care sample testing are assigned to the same assignee as the present application: DISPOSABLE SENSING DEVICE FOR REAL TIME FLUID ANALYSIS, Lauks et al., U.S. Pat. No. 5,096,669; WHOLLY MICROFABRICATED BIOSENSORS AND PROCESS FOR THE MANUFACTURE AND USE THEREOF, Cozzette et al., U.S. Pat. No. 5,200,051; METHOD FOR ANALYTICALLY UTILIZING MICROFABRICATED SENSORS DURING WET-UP, Cozzette et al., U.S. Pat. No. 5,112,455; SYSTEM, METHOD AND COMPUTER IMPLEMENTED PROCESS FOR ASSAYING COAGULATION IN FLUID SAMPLES, Opalsky et al., U.S. Pat. No. 6,438,498; MICROFABRICATED APERTURE-BASED SENSOR, Davis et al., U.S. Pat. No. 6,379,883; APPARATUS FOR ASSAYING VISCOSITY CHANGES IN FLUID SAMPLES AND METHOD OF CONDUCTING SAME, Davis et al., U.S. Pat. No. 5,447,440; REUSABLE TEST UNIT FOR SIMULATING ELECTROCHEMICAL SENSOR SIGNALS FOR QUALITY ASSURANCE OF PORTABLE BLOOD ANALYZER INSTRUMENTS, Zelin et al., U.S. Pat. No. 5,124,661; STATIC-FREE INTERROGATING CONNECTOR FOR ELECTRICAL COMPONENTS, Lauks U.S. Pat. No. 4,954,087; and REFERENCE ELECTRODE, METHOD OF MAKING AND METHOD OF USING SAME, Lauks, U.S. Pat. No. 4,933,048, the entire contents of each of which are hereby incorporated by reference herein.

However, as patients can be on a medical therapy delivery system, such as a ventilator or the like, at the time the medical sample is taken, how such medical therapy delivery systems are set up can affect the interpretation of, for example, the blood gas and other analysis results provided by the analyzer or reading apparatus. Thus, there is a need for a system that can use or otherwise incorporate the operating parameters of the medical therapy delivery system in the analysis of the medical sample to provide a better interpretation of the blood gas and other sample analysis results.

SUMMARY OF THE INVENTION

A sample analysis and medical data acquisition system and method for patient management are disclosed. In accordance with exemplary embodiments of the present invention, according to a first aspect of the present invention, a sample analysis and medical data acquisition system for patient management includes a first user interface display module. The first user interface display module is configured to display a medical chart page. The medical chart page includes at least one selectable item associated with patient management. One of the at least one selectable item includes a medical delivery selection. The first user interface display module is further configured to display a set of medical delivery systems associated with the medical delivery selection from the medical chart page. A medical delivery system is chosen from the set of medical delivery systems. The system includes a second user interface display module in communication with the first user interface display module. The second user interface display module is configured to display parameter fields for entry of operation data associated with the chosen medical delivery system. Medical data is captured from a patient by an analyzer configured to perform an analysis of a sample from the patient. The medical data is analyzed in accordance with entered operation data. The system includes an analysis display module in communication with at least the first user interface display module. The analysis display module is configured to display sample analysis results of the medical data analyzed in accordance with the entered operation data.

According to the first aspect, the sample can comprise, for example, blood, serum, plasma, urine, saliva, cheek swab, cerebrospinal fluid or any other suitable type of sample from a patient. The analysis display module can be configured to display the medical data along with the sample analysis results. The system can include a third user interface display module in communication with at least the first user interface display module. The third user interface display module can be configured to display a mode selection list associated with the chosen medical delivery system. A mode can be chosen from the mode selection list. The second user interface display can be configured to display the parameter fields in accordance with the chosen mode for entry of the operation data. The system can include a patient data display module in communication with at least the first user interface display module. The patient data display module can be configured to display medical data associated with each patient. The first user interface display module can be configured to display a plurality of medical chart pages. Each of the plurality of medical chart pages can be associated with an analyzer cartridge. The first user interface display module can be configured to display the medical chart page in accordance with the analyzer cartridge being used with the analyzer.

According to the first aspect, the system can include a medical chart page manager module in communication with at least the first user interface display module. The medical chart page manager module can be configured to assign medical chart pages to analyzer cartridge types. The medical chart page manager module can be configured to assign medical chart pages to operation data associated with each medical delivery system. The medical chart page manager module can be configured to assign medical chart pages to medical data associated with each patient. The medical chart page can further include at least one parameter field for entry of medical data associated with the patient. The medical chart page can be configured to display the chosen medical delivery system. The medical chart page can be customizable in accordance with a location of use of the sample analysis and medical data acquisition system. The location can comprise a location within a hospital. For example, the location within the hospital can comprise an intensive care unit, a critical care unit, a general ward, an operating room, an emergency department or other suitable location within a hospital or medical care facility. The medical chart page can be customizable in accordance with an analyzer cartridge. For example, the analyzer cartridge can comprise a disposable biological fluid analysis cartridge or the like. The first and second user interface display modules and the analysis display module can be configured to display information via the analyzer. According to an alternative exemplary embodiment of the first aspect, the first and second user interface display modules and the analysis display module can be configured to display information via a display screen.

According to the first aspect, the system can include the analyzer. For example, the analyzer can comprise a portable point-of-care biological fluid analysis device. According to an alternative exemplary embodiment of the first aspect, the sample analysis and medical data acquisition system can be in communication with the analyzer using any suitable communication medium and/or protocol. The system can include a storage module in communication with at least the first user interface display module. The storage module can be configured to store at least one of the operation data and the sample analysis results for each patient. The medical delivery system can comprise, for example, a respiratory delivery system or the like. For example, the respiratory delivery system can comprise a ventilator, and the operation data can comprise ventilator machine settings.

According to a second aspect of the present invention, a method of analyzing patient samples and acquiring medical data for managing patients includes the steps of: a.) displaying a medical chart page, in which the medical chart page comprises at least one selectable item associated with patient management, and in which one of the at least one selectable item comprises a medical delivery selection; b.) selecting the medical delivery selection from the medical chart page; c.) displaying a set of medical delivery systems associated with the medical delivery selection from the medical chart page; d.) choosing a medical delivery system from the set of medical delivery systems; e.) displaying parameter fields for entry of operation data associated with the chosen medical delivery system; f.) analyzing medical data captured from a patient in accordance with entered operation data; and g.) displaying patient sample analysis results for the medical data analyzed in accordance with the entered operation data.

According to the second aspect, the patient sample can comprise, for example, blood, serum, plasma, urine, saliva, cheek swab, cerebrospinal fluid, or any other suitable type of patient sample. Step (g) can include the step of: g1.) displaying the medical data along with the patient sample analysis results. Step (d) can include the steps of: d1.) displaying a mode selection list associated with the chosen medical delivery system; and d2.) choosing a mode from the mode selection list; and step (e) can include the step of: e1.) displaying the parameter fields in accordance with the chosen mode for entry of the operation data. The method can include the step of: h.) displaying medical data associated with each patient. According to an exemplary embodiment of the second aspect, medical chart pages can be assigned to analyzer cartridge types, and the method can comprise the step of: i.) displaying the medical chart page assigned to an analyzer cartridge type being used. According to an alternative exemplary embodiment of the second aspect, the medical chart pages can be assigned to operation data associated with each medical delivery system, and the method can comprise the step of: j.) displaying the medical chart page assigned to the operation data associated with the chosen medical delivery system. According to another alternative exemplary embodiment of the second aspect, the medical chart pages can be assigned to medical data associated with each patient, and the method can comprise the step of: k.) displaying the medical chart page assigned to the medical data associated with the patient.

According to the second aspect, the medical chart page can further comprise at least one parameter field for entry of medical data associated with the patient. The method can include the step of: l.) displaying the chosen medical delivery system in the medical chart page. The medical chart page(s) can be customizable in accordance with the location of use. The location can comprise, for example, a location within a hospital or other medical care facility. For example, the location within the hospital can comprise an intensive care unit, a critical care unit, a general ward, an operating room, an emergency department or other like location within the hospital or medical care facility. According to an alternative exemplary embodiment of the second aspect, the medical chart page can be customizable in accordance with an analyzer cartridge. For example, the analyzer cartridge can comprise a disposable biological fluid analysis cartridge. Step (f) can be conducted by an analyzer configured to perform an analysis of the patient sample from the patient. According to an exemplary embodiment of the second aspect, steps (a), (c), (e) and (g) can be configured to display information via the analyzer. For example, the analyzer can comprise a portable point-of-care biological fluid analysis device or other like device. According to an alternative exemplary embodiment of the second aspect, steps (a), (c), (e) and (g) can be configured to display information via a display screen. The method can include the step of: m.) storing at least one of the operation data and the patient sample analysis results for each patient. The medical delivery system can comprise a respiratory delivery system or other like system. For example, the respiratory delivery system can comprise a ventilator, and the operation data can comprise ventilator machine settings.

According to a third aspect of the present invention, a sample analysis and medical data acquisition system for patient management includes a first means for displaying a user interface. The first user interface displaying means can be configured to display a medical chart page. The medical chart page comprises at least one selectable item associated with patient management. One of the at least one selectable item comprises a medical delivery selection. The first user interface displaying means is further configured to display a set of medical delivery systems associated with the medical delivery selection from the medical chart page. A medical delivery system is chosen from the set of medical delivery systems. The system includes a second means for displaying a user interface in communication with the first user interface displaying means. The second user interface displaying means is configured to display parameter fields for entry of operation data associated with the chosen medical delivery system. Medical data is captured from a patient by an analyzer means configured to perform an analysis of a sample from the patient. The medical data is analyzed in accordance with entered operation data. The system includes means for displaying an analysis in communication with the first and second user interface displaying means. The analysis displaying means is configured to display sample analysis results of the medical data analyzed in accordance with the entered operation data.

According to the third aspect, the sample can comprise blood, serum, plasma, urine, saliva, cheek swab, cerebrospinal fluid, or any other suitable type of sample from a patient. The analysis displaying means can be configured to display the medical data along with the sample analysis results. The system can include a third means for displaying a user interface in communication with the first and second user interface displaying means. The third user interface displaying means can be configured to display a mode selection list associated with the chosen medical delivery system. A mode can be chosen from the mode selection list. The second user interface displaying means can be configured to display the parameter fields in accordance with the chosen mode for entry of the operation data. The system can include means for displaying patient data in communication with the first and second user interface displaying means and the analysis displaying means. The patient data displaying means is configured to display medical data associated with each patient. The first user interface displaying means can be configured to display a plurality of medical chart pages. Each of the plurality of medical chart pages can be associated with an analyzer cartridge. The first user interface displaying means can be configured to display the medical chart page in accordance with the analyzer cartridge being used with the analyzer means.

According to the third aspect, the system can include means for managing medical chart pages in communication with the first and second user interface displaying means and the analysis displaying means. According to an exemplary embodiment of the third aspect, the medical chart page managing means can be configured to assign medical chart pages to analyzer cartridge types. According to an alternative exemplary embodiment of the third aspect, the medical chart page managing means can be configured to assign medical chart pages to operation data associated with each medical delivery system. According to another alternative exemplary embodiment of the third aspect, the medical chart page managing means can be configured to assign medical chart pages to medical data associated with each patient. The medical chart page can further comprise at least one parameter field for entry of medical data associated with the patient. The medical chart page can be configured to display the chosen medical delivery system. The medical chart page can be customizable in accordance with the location of use of the sample analysis and medical data acquisition system. The location can comprise, for example, a location within a hospital or other medical care facility. For example, the location within the hospital can comprise an intensive care unit, a critical care unit, a general ward, an operating room, an emergency department or other suitable location within the hospital or medical care facility. The medical chart page can be customizable in accordance with an analyzer cartridge. For example, the analyzer cartridge can comprise a disposable biological fluid analysis cartridge or the like.

According to the third aspect, the first and second user interface displaying means and the analysis displaying means can be configured to display information via the analyzer means. According to an alternative exemplary embodiment of the third aspect, the first and second user interface displaying means and the analysis displaying means are configured to display information via a means for displaying information. The system can comprise the analyzer means. For example, the analyzer means can comprise a portable point-of-care biological fluid analysis means or other like means. According to an alternative exemplary embodiment of the third aspect, the sample analysis and medical data acquisition system can be in communication with the analyzer means using any suitable type of communication medium and/or protocol. The system can include means for storing information in communication with at least the first user interface displaying means. The information storing means can be configured to store the operation data and/or the sample analysis results for each patient, as well as other suitable patient management information. The medical delivery system can comprise a respiratory delivery system or other like device. For example, the respiratory delivery system can comprise a ventilator, and the operation data can comprise ventilator machine settings.

According to a fourth aspect of the present invention, a computer-readable medium contains a computer program for analyzing patient samples and acquiring medical data for managing patients. The computer program performs the steps of: a.) generating a display for a medical chart page, in which the medical chart page comprises at least one selectable item associated with patient management, and in which one of the at least one selectable item comprises a medical delivery selection; b.) receiving an indication of a selection of the medical delivery selection from the medical chart page; c.) generating a display for a set of medical delivery systems associated with the medical delivery selection from the medical chart page in response to step (b); d.) receiving an indication of a choice of a medical delivery system from the set of medical delivery systems; e.) generating a display for parameter fields for entry of operation data associated with the chosen medical delivery system in response to step (d); f.) analyzing medical data captured from a patient in accordance with entered operation data; and g.) generating a display for patient sample analysis results for the medical data analyzed in accordance with the entered operation data in response to step (f). According to an exemplary embodiment of the fourth aspect, the patient sample can comprise, for example, blood, serum, plasma, urine, saliva, cheek swab, cerebrospinal fluid or any other suitable type of patient sample.

According to a fifth aspect of the present invention, a sample analysis and medical data acquisition system for patient management includes a memory that stores steps of a computer program to: a.) generate a display for a medical chart page, in which the medical chart page comprises at least one selectable item associated with patient management, and in which one of the at least one selectable item comprises a medical delivery selection; b.) receive an indication of a selection of the medical delivery selection from the medical chart page; c.) generate a display for a set of medical delivery systems associated with the medical delivery selection from the medical chart page in response to step (b); d.) receive an indication of a choice of a medical delivery system from the set of medical delivery systems; e.) generate a display for parameter fields for entry of operation data associated with the chosen medical delivery system in response to step (d); f.) analyze medical data captured from a patient in accordance with entered operation data; and g.) generate a display for sample analysis results of the medical data analyzed in accordance with the entered operation data in response to step (f). The system also includes a processor for accessing the memory to execute the steps. According to an exemplary embodiment of the fifth aspect, the sample can comprise, for example, blood, serum, plasma, urine, saliva, cheek swab, cerebrospinal fluid, or any other suitable type of sample from a patient.

According to a sixth aspect of the present invention, a medical data acquisition and patient management system includes a first user interface display module. The first user interface display module is configured to display a medical chart page. The medical chart page comprises at least one selectable item associated with patient management. One of the at least one selectable item comprises a medical therapy delivery selection. The system includes a second user interface display module in communication with the first user interface display module. The second user interface display module is configured to display a list of medical therapy delivery systems associated with the medical therapy delivery selection from the medical chart page. A medical therapy delivery system is chosen from the list of medical therapy delivery systems. The system includes a third user interface display module in communication with at least the first user interface display module. The third user interface display module is configured to display parameter fields for entry of operation data associated with the chosen medical therapy delivery system. Medical data captured from a patient by a medical analyzer is analyzed in accordance with the operation data.

According to the sixth aspect, the medical data can comprise information associated with, for example, a blood sample, a serum sample, a plasma sample, a urine sample, a saliva sample, a cheek swab sample, a cerebrospinal fluid sample, or any other suitable type of sample from a patient. The system can include a fourth user interface display module in communication with at least the first user interface display module. The fourth user interface display module can be configured to display a mode selection list associated with the chosen medical therapy delivery system. A mode can be chosen from the mode selection list. The third user interface display module can be configured to display the parameter fields in accordance with the chosen mode for entry of the operation data. The system can include an analysis display module in communication with at least the first user interface display module. The analysis display module can be configured to display analysis results of the medical data analyzed in accordance with the operation data. The system can include a patient data display module in communication with at least the first user interface display module. The patient data display module can be configured to display medical data associated with each patient. The first user interface display module can be configured to display a plurality of medical chart pages. Each of the plurality of medical chart pages can be associated with a medical analyzer cartridge or the like. For example, the first user interface display module can be configured to display the medical chart page in accordance with the medical analyzer cartridge being used with the medical analyzer.

According to the sixth aspect, the system can include a medical chart page manager module in communication with at least the first user interface display module. According to an exemplary embodiment of the sixth aspect, the medical chart page manager module can be configured to assign medical chart pages to medical analyzer cartridge types. According to an alternative exemplary embodiment of the sixth aspect, the medical chart page manager module can be configured to assign medical chart pages to operation data associated with each medical therapy delivery system. According to another alternative exemplary embodiment of the sixth aspect, the medical chart page manager module can be configured to assign medical chart pages to medical data associated with each patient. The medical chart page can further comprise at least one parameter field for entry of medical data associated with the patient. The medical chart page can be configured to display the chosen medical therapy delivery system. According to an exemplary embodiment of the sixth aspect, the medical chart page can be customizable in accordance with, for example, a location of use of the medical data acquisition and patient management system. For example, the location can comprise a location within a hospital or other medical care facility. The location within the hospital can comprise an intensive care unit, a critical care unit, a general ward, an operating room, an emergency department or other suitable location within the hospital or medical care facility. According to an alternative exemplary embodiment of the sixth aspect, the medical chart page can be customizable in accordance with a medical analyzer cartridge. For example, the medical analyzer cartridge can comprise a disposable biological fluid analysis cartridge or the like.

According to an exemplary embodiment of the sixth aspect, the first, second and third user interface display modules can be configured to display information via the medical analyzer. According to an alternative exemplary embodiment of the sixth aspect, the first, second and third user interface display modules can be configured to display information via a display screen. The system can comprise the medical analyzer. For example, the medical analyzer can comprise a portable point-of-care biological fluid analysis device or other like device. Alternatively, the medical data acquisition and patient management system can be in communication with the medical analyzer using any suitable communication medium and/or protocol. The system can include a storage module in communication with at least the first user interface display module. The storage module can be configured to store the operation data and/or the analyzed medical data for each patient, as well as other suitable information for patient management. The medical therapy delivery system can comprise a respiratory delivery system or the like. For example, the respiratory delivery system can comprise a ventilator, and the operation data can comprise ventilator machine settings.

According to a seventh aspect of the present invention, a method of acquiring medical data and managing patients includes the steps of: a.) displaying a medical chart page, in which the medical chart page comprises at least one selectable item associated with patient management, and in which one of the at least one selectable item comprises a medical therapy delivery selection; b.) selecting the medical therapy delivery selection from the medical chart page; c.) displaying a list of medical therapy delivery systems associated with the medical therapy delivery selection from the medical chart page; d.) choosing a medical therapy delivery system from the list of medical therapy delivery systems; e.) displaying parameter fields for entry of operation data associated with the chosen medical therapy delivery system; and f.) analyzing medical data captured by a medical analyzer from a patient in accordance with the operation data.

According to the seventh aspect, the medical data can comprise information associated with, for example, a blood sample, a serum sample, a plasma sample, a urine sample, a saliva sample, a cheek swab sample, a cerebrospinal fluid sample, or any other suitable type of sample from a patient. Step (d) can comprise the steps of: d1.) displaying a mode selection list associated with the chosen medical therapy delivery system; and d2.) choosing a mode from the mode selection list; and in which step (e) can comprise the step of: e1.) displaying the parameter fields in accordance with the chosen mode for entry of the operation data. The method can include the steps of: g.) displaying analysis results of the medical data analyzed in accordance with the operation data; and g.) displaying medical data associated with each patient. The method can include the steps of: g.) displaying a plurality of medical chart pages, in which each of the plurality of medical chart pages is associated with a medical analyzer cartridge; and h.) displaying the medical chart page in accordance with the medical analyzer cartridge being used with the medical analyzer. The method can include the steps of: g.) assigning medical chart pages to medical analyzer cartridge types; g.) assigning medical chart pages to operation data associated with each medical therapy delivery system; and/or g.) assigning medical chart pages to medical data associated with each patient. The medical chart page can further comprise at least one parameter field for entry of medical data associated with the patient. The method can include the step of: g.) displaying the chosen medical therapy delivery system in the medical chart page.

According to the seventh aspect, the medical chart page can be customizable in accordance with a location of use. The location can comprise, for example, a location within a hospital or other medical care facility. For example, the location within the hospital can comprise an intensive care unit, a critical care unit, a general ward, an operating room, an emergency department or other suitable location within the hospital or medical care facility. The medical chart page can be customizable in accordance with a medical analyzer cartridge. For example, the medical analyzer cartridge can comprise a disposable biological fluid analysis cartridge or the like. The method can include the step of: g.) displaying information via the medical analyzer. According to an alternative exemplary embodiment of the seventh aspect, the method can include the step of: g.) displaying information via a display screen. The medical analyzer can comprise, for example, a portable point-of-care biological fluid analysis device or other like device. The method can include the step of: g.) storing at least one of the operation data and the analyzed medical data for each patient. The medical therapy delivery system can comprise a respiratory delivery system or other like system or device. For example, the respiratory delivery system can comprise a ventilator, and the operation data can comprise ventilator machine settings.

According to an eighth aspect of the present invention, a medical data acquisition and patient management system includes a first means for displaying a user interface. The first user interface displaying means is configured to display a medical chart page. The medical chart page comprises at least one selectable item associated with patient management. One of the at least one selectable item comprises a medical therapy delivery selection. The system includes a second means for displaying a user interface in communication with the first user interface displaying means. The second user interface displaying means is configured to display a list of means for delivering medical therapy associated with the medical therapy delivery selection from the medical chart page. A medical therapy delivering means is chosen from the list of medical therapy delivering means. The system includes a third means for displaying a user interface in communication with the first and second user interface displaying means. The third user interface displaying means is configured to display parameter fields for entry of operation data associated with the chosen medical therapy delivering means. Medical data captured from a patient by a medical analyzer means is analyzed in accordance with the operation data. According to an exemplary embodiment of the eighth aspect, the medical data can comprise information associated with, for example, a blood sample, a serum sample, a plasma sample, a urine sample, a saliva sample, a cheek swab sample, a cerebrospinal fluid sample, or any other suitable type of sample from a patient.

According to a ninth aspect of the present invention, a computer-readable medium contains a computer program for acquiring medical data and managing patients. The computer program performs the steps of: a.) displaying a medical chart page, in which the medical chart page comprises at least one selectable item associated with patient management, and in which one of the at least one selectable item comprises a medical therapy delivery selection; b.) receiving a first signal indicating a selection of the medical therapy delivery selection from the medical chart page; c.) displaying a list of medical therapy delivery systems associated with the medical therapy delivery selection from the medical chart page in response to step (b); d.) receiving a second signal indicating a choice of a medical therapy delivery system from the list of medical therapy delivery systems; e.) displaying parameter fields for entry of operation data associated with the chosen medical therapy delivery system in response to step (d); and f.) analyzing medical data captured by a medical analyzer from a patient in accordance with the operation data. According to an exemplary embodiment of the ninth aspect, the medical data can comprise information associated with, for example, a blood sample, a serum sample, a plasma sample, a urine sample, a saliva sample, a cheek swab sample, a cerebrospinal fluid sample or any other suitable type of sample from a patient.

According to a tenth aspect of the present invention, a medical data acquisition and patient management system includes a memory that stores steps of a computer program to: a.) generate a display for a medical chart page, in which the medical chart page comprises at least one selectable item associated with patient management, and in which one of the at least one selectable item comprises a medical therapy delivery selection; b.) receive a first signal indicating a selection of the medical therapy delivery selection from the medical chart page; c.) generate a display for a list of medical therapy delivery systems associated with the medical therapy delivery selection from the medical chart page in response to step (b); d.) receive a second signal indicating a choice of a medical therapy delivery system from the list of medical therapy delivery systems; e.) generate a display for parameter fields for entry of operation data associated with the chosen medical therapy delivery system in response to step (d); and f.) analyze medical data captured by a medical analyzer from a patient in accordance with the operation data. The system also includes a processor for accessing the memory to execute the steps. According to an exemplary embodiment of the tenth aspect, the medical data can comprise information associated with, for example, a blood sample, a serum sample, a plasma sample, a urine sample, a saliva sample, a cheek swab sample, a cerebrospinal fluid sample or any other suitable type of sample from a patient.

According to an eleventh aspect of the present invention, a medical data acquisition and patient management system includes a first user interface display module. The first user interface display module is configured to display a medical chart page. The medical chart page comprises at least one selectable item associated with patient management. One of the at least one selectable item comprises a medical instrumentation selection. The first user interface display module is further configured to display a list of medical instrumentation devices associated with the medical instrumentation selection from the medical chart page. A medical instrumentation device is chosen from the list of medical instrumentation devices. The system includes a second user interface display module in communication with the first user interface display modules. The second user interface display module is configured to display parameter fields for entry of operation data associated with the chosen medical instrumentation device. Medical data captured from a patient by a medical data capture device is analyzed in accordance with the operation data. According to an exemplary embodiment of the eleventh aspect, the medical data can comprise information associated with, for example, a blood sample, a serum sample, a plasma sample, a urine sample, a saliva sample, a cheek swab sample, a cerebrospinal fluid sample, or any other suitable type of sample from a patient.

BRIEF DESCRIPTION OF THE DRAWINGS

Other objects and advantages of the present invention will become apparent to those skilled in the art upon reading the following detailed description of preferred embodiments, in conjunction with the accompanying drawings, wherein like reference numerals have been used to designate like elements, and wherein:

FIG. 4A is a diagram illustrating a customized medical chart page with the first five medical chart page items completed and the delivery system selection list item highlighted, in accordance with an exemplary embodiment of the present invention.

FIG. 4B is a diagram illustrating a selection list page of available medical delivery system choices corresponding to the delivery system selection list item illustrated in FIG. 4A, in accordance with an exemplary embodiment of the present invention.

FIG. 4C is a diagram illustrating a parameter page displaying the parameter fields for entry of the operation data associated with the delivery system chosen from the selection list page of FIG. 4B, in accordance with an exemplary embodiment of the present invention.

FIG. 4D is a diagram illustrating the medical chart page displaying the selected medical delivery system of "Venti-Mask," in accordance with an exemplary embodiment of the present invention.

DETAILED DESCRIPTION OF THE PREFERRED EMBODIMENTS

Exemplary embodiments of the present invention are directed to a system and method for sample analysis and medical data acquisition for patient management. A medical analyzer or other like device can be used to analyze samples and other like medical data taken or otherwise captured from a patient. However, as patients can be on a medical therapy delivery system, such as a ventilator or the like, at the time the medical data or sample is taken, how such medical therapy delivery systems are set up can affect the interpretation of, for example, the blood gas and other analysis results obtained from a blood sample provided by the medical analyzer. According to exemplary embodiments, a menu-driven system is configured to allow the input of settings and other operating parameters for the medical therapy delivery system. The operating parameters are then used in the analysis of the medical data or sample to provide a better interpretation of such patient samples. According to exemplary embodiments, the samples can comprise, for example, blood, serum, plasma, urine, saliva, cheek swab, cerebrospinal fluid, or any other suitable type of sample that can be taken from a patient.

Figure 1A:
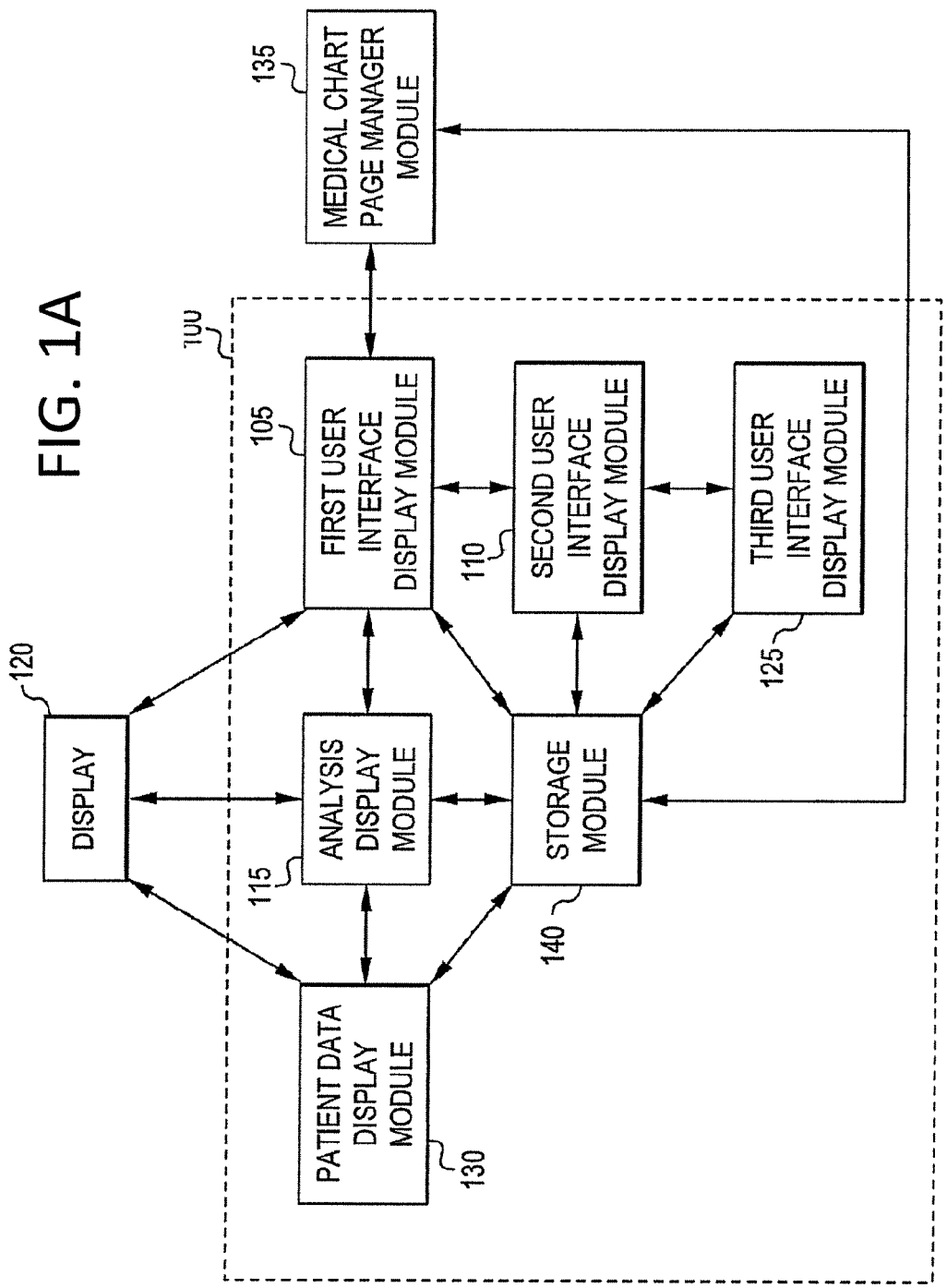
FIGS. 1A and 1B are diagrams illustrating a system for sample analysis and medical data acquisition for patient management, in accordance with an exemplary embodiment of the present invention.

These and other aspects and embodiments of the present invention will now be described in greater detail. FIG. 1A is a diagram illustrating a system 100 for sample analysis and medical data acquisition for patient management, in accordance with an exemplary embodiment of the present invention. The system 100 includes a first user interface display module 105 that is configured to generate and display one or more medical chart pages. As used herein, a "page" can comprise any suitably viewable or otherwise displayable layout or user interface of textual and/or graphical information. Consequently, a "medical chart page" can comprise a page that can include any suitable medical and/or other data associated with a patient(s) and management of the patient(s). The medical chart pages can be customized to suit various data recording needs by providing customizable data entry items and selection list items. According to an exemplary embodiment, the medical chart page can include at least one selectable item associated with patient management. For example, the at least one selectable item can comprise a medical delivery selection.

Figure 2:
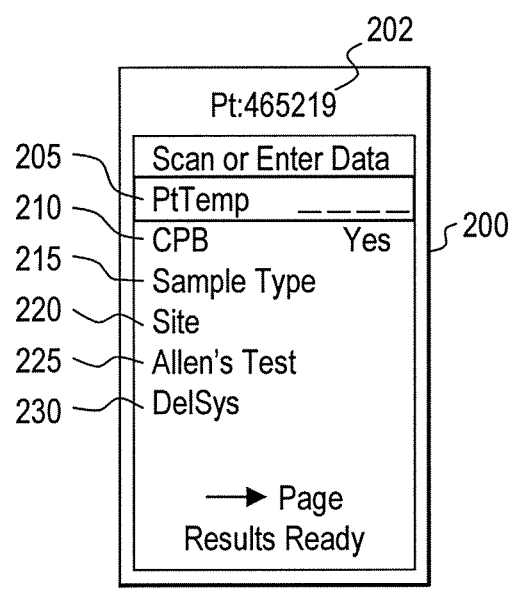
FIG. 2 is a diagram illustrating a customized medical chart page for patient management, in accordance with an exemplary embodiment of the present invention.

For purposes of illustration and not limitation, FIG. 2 is a diagram illustrating a customized medical chart page 200 for patient management, in accordance with an exemplary embodiment of the present invention. In the present illustration, the medical chart page 200 includes one data entry item and five selection list items, although each medical chart page 200 can include any suitable number and combination of data entry items and selection list items or other appropriate types of information. For the medical chart page 200, data entry items, such as, for example, data entry item 205 ("PtTemp"—patient temperature), can allow a user to scan or otherwise enter alphanumeric data using a suitable data input device (e.g., keyboard, keypad, mouse, scanner, or other like data entry or input device or mechanism). Selection list items, such as, for example, selection list items 210 ("CPB"—Cardio-Pulnonary Bypass), 215 ("Sample Type"), 220 ("Site"—Draw Site), 225 ("Allen's Test") and 230 ("DelSys"—delivery system), can allow a user to select from a customized list of choices. Each medical chart page 200 can include a suitable patient identifier 202 (e.g., "Pt:465219" or other appropriate patient identification) located, for example, at the top or other suitable location within the medical chart page 200.

Figures 3A, 3B, 3C:
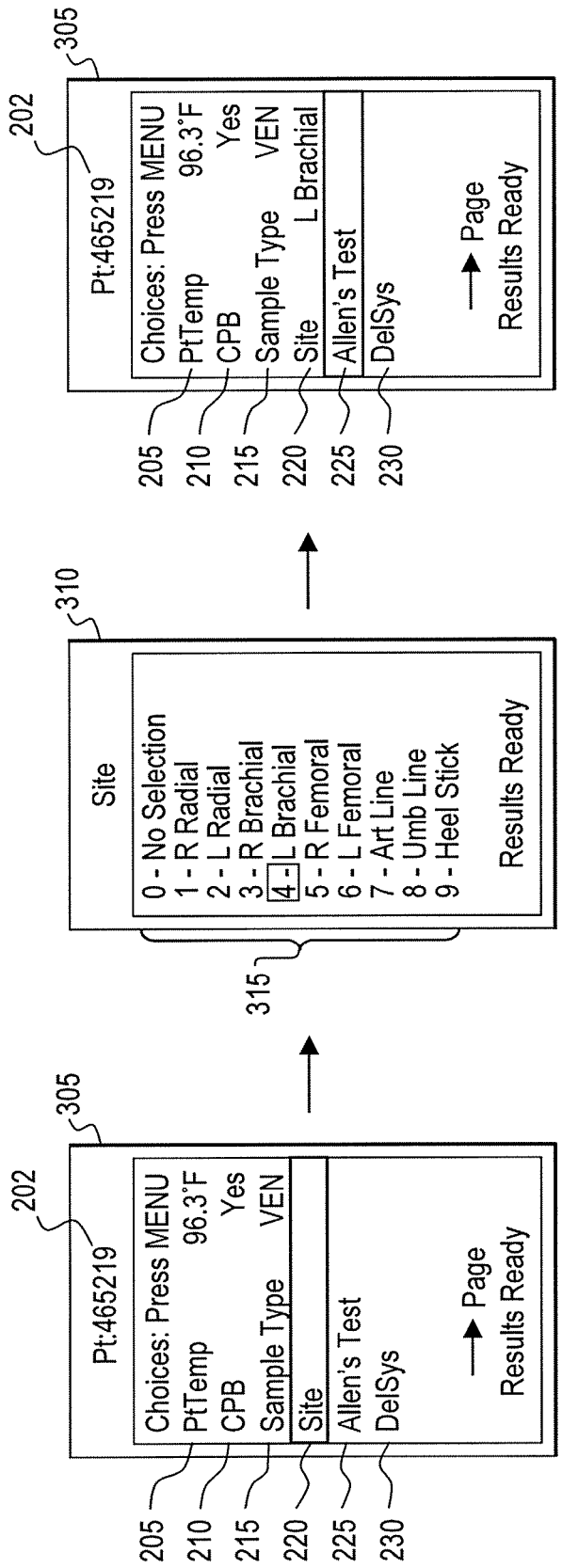
FIG. 3A is a diagram illustrating a customized medical chart page with the first three medical chart page items completed and the site selection list item highlighted, in accordance with an exemplary embodiment of the present invention.
FIG. 3B is a diagram illustrating a selection list page of available draw site choices corresponding to the draw site selection item illustrated in FIG. 3A, in accordance with an exemplary embodiment of the present invention.
FIG. 3C is a diagram illustrating the customized medical chart page displaying the chosen selection for the draw site, in accordance with an exemplary embodiment of the present invention.

For purposes of illustration and not limitation, FIG. 3A is a diagram illustrating a customized medical chart page 305 with the first three medical chart page items (data entry item 205 and selection list items 210 and 215) of medical chart page 200 completed and the site selection list item 220 highlighted, in accordance with an exemplary embodiment of the present invention. By appropriately selecting a selection list item (e.g., via a suitable key or key combination, such as a "Menu" or "Enter" key, via a finger or stylus, via a mouse or other data input device, or other like means), the available choices for that selection list item can be displayed. Alternatively, the available choices for the given selection list item can be automatically displayed to the user, for example, by automatically displaying the available choices in a pop-up window or the like when a selection list item is highlighted or otherwise selected (e.g., moving the mouse cursor over the selection list item). According to an exemplary embodiment, the first user interface display module 105 can be configured to display the set or list of available choices associated with the given selection list item from the medical chart page 200. The list of available choices can be displayed in any suitable manner, such as, for example, on a separate page, within the medical chart page (e.g., as a subpage or partition of the medical chart page), as a pop-up or pull-down menu of choices, or in any other appropriate manner.

For example, FIG. 3B is a diagram illustrating a site choice or selection list page 310 of available draw site choices corresponding to the draw site selection item 220 illustrated in FIG. 3A, in accordance with an exemplary embodiment of the present invention. Each of the draw sites 315 can be listed or otherwise displayed in any suitable manner in the selection list page 310. For example, each draw site 315 can be associated with an alphanumeric designation (e.g., "0" for "No Selection," "1" for "Right Radial," "2" for "Left Radial," "3" for "Right Brachial," . . . , "9" for "Heel Stick") or other suitable designator. Accordingly, pressing the corresponding alphanumeric key of the data input device or otherwise selecting the appropriate alphanumeric designation can select the desired choice from the list of draw sites 315. For example, selecting the numeral "4" from the list of draw sites 315 can select "L Brachial" (i.e., left brachial) as the desired draw site. The selected choice can then be displayed to the user in any suitable manner. For example, FIG. 3C is a diagram illustrating the customized medical chart page 305 displaying the chosen selection for the draw site, in accordance with an exemplary embodiment of the present invention. In other words, upon selection of the desired draw site 315 from the selection list page 310 of FIG. 3B, the user can be returned to the medical chart page 305 with the selected draw site (e.g., "L Brachial") appearing near or beside the site selection list item 220 prompt, as illustrated in FIG. 3C.

Referring to FIG. 1A, the system 100 includes a second user interface display module 110 in communication with at least the first user interface display module 105. The second user interface display module 110 is configured to generate and display parameter fields for entry of operation data associated with a chosen medical delivery system. As used herein, a "medical delivery system" can be any suitable machine or other device, system, plan or regiment capable of delivering medical therapy to a patient. For example, medical delivery systems can include, but are not limited to: a respiratory delivery system, such as a ventilator or the like; a machine capable of delivering anesthetic gases as operated by an anesthetist; an intravenous drug delivery system; a cardiac bypass machine that can be used to replace the function of the heart and lungs during heart surgery; a machine providing radiation therapy; an insulin pump for subcutaneous insulin delivery (optionally worn by a patient); a machine for cooling a patient's core body temperature during a surgical procedure; a dialysis machine for removing metabolic waste products from patients with impaired kidney function; a machine for providing light therapy in combination with drugs that require in vivo light activation; a machine, device, system, plan or regiment that is medical delivery or treatment related or derived from molecular biology or the like; or any other suitable machine or device capable of delivering medical therapy. For example, if the medical delivery system comprises a respiratory delivery system, such as a ventilator, then the operation data can comprise ventilator machine settings. It is noted that parameters or operation data can be obtained from one or more medical delivery systems to derive a complete patient data set.

According to exemplary embodiments, the entry of operation data associated with a chosen medical delivery system can be performed either manually by the user or automatically by the system 100. For automatic entry, for example, a medical chart page can be presented to the user, and an item for a medical delivery system can be highlighted or otherwise selected by the user. Upon selection, the appropriate module of the system 100 can initiate and cause to be transmitted (e.g., out a serial port of an appropriate analyzer) a suitable request to the medical delivery system for the operation data. Alternatively, the request can be sent to any other appropriate system that can provide the operation data for or on behalf of the chosen medical delivery system. The medical delivery or other system can then respond with, for example, an identification number or other identifying information for the chosen medical delivery system, and the operation data or other parameters associated with the chosen medical delivery system.

Returning to FIG. 2, according to exemplary embodiments, customization of the medical chart pages also provides the ability to create unique medical delivery system parameter entry pages that can appear depending on the selection of the medical delivery system defined by the delivery system selection list item 230 of medical chart page 200. For purposes of illustration and not limitation, FIG. 4A is a diagram illustrating a customized medical chart page 405 with the first five medical chart page items (data entry item 205 and selection list items 210, 215, 220 and 225) of medical chart page 200 completed and the delivery system selection list item 230 highlighted, in accordance with an exemplary embodiment of the present invention. By appropriately selecting the delivery system selection list item 230, the available choices for that selection list item can be displayed. According to an exemplary embodiment, the first user interface display module 105 can be configured to display the set or list of medical delivery systems associated with the medical delivery selection (e.g., delivery system selection list item 230) from the medical chart page 405.

For example, FIG. 4B is a diagram illustrating a delivery system choice or selection list page 410 of available medical delivery system choices corresponding to the delivery system selection list item 230 illustrated in FIG. 4A, in accordance with an exemplary embodiment of the present invention. Each of the delivery system choices 415 can be listed or otherwise displayed in any suitable manner (e.g., by the first user interface display module 105) in the selection list page 410. In addition, the selection list choices (e.g., the delivery system choices) are fully customizable according to the needs of the user and the environment in which the system 100 is to be used. For example, each delivery system choice 415 can be associated with an alphanumeric designation (e.g., "0" for "No Selection," "1" for "Room Air," "2" for "Nasal Can," "3" for "Bagging," . . . , "9" for "AerosolMsk") or other suitable designator. Accordingly, pressing the corresponding alphanumeric key of the data input device or otherwise selecting the appropriate alphanumeric designation can select the desired choice from the list of delivery system choices 415. Thus, the user can choose a medical delivery system from the set or list of delivery system choices 415 displayed in selection list page 410. For example, selecting the numeral "5" from the list of delivery system choices 415 can select "VentiMask" as the desired medical delivery system, and the user can then be moved to a parameter entry page corresponding to the chosen medical delivery system. As will be apparent to those skilled in respiratory therapy management, the abbreviations used here correspond to well-known delivery system settings (e.g., "Nasal Can" corresponds to "Nasal Cannula," "AerosolMsk" corresponds to "Aerosol Mask," "VentiMask" corresponds to "Venturi Mask," and the like).

For purposes of illustration and not limitation, FIG. 4C is a diagram illustrating a parameter page 420 displaying the parameter fields 425 for entry of the operation data associated with the delivery system chosen from the selection list page 410 of FIG. 4B, in accordance with an exemplary embodiment of the present invention. Through the parameter page 420, the required parameters or other operation data can be entered for the chosen medical delivery system using a suitable data input device (e.g., "IT" representing "Inspiratory Time," "RR" representing "Respiratory Time," "Vt" representing "Tidal Volume," and "FIO2" representing "Fractional Inspired Oxygen" or any other suitable parameter information, depending on the type of medical delivery system chosen). Upon entry of the parameters or other operation data, the user can be returned to the medical chart page 405 (of FIG. 4A) with the selected medical delivery system (e.g., "Venti-Mask") appearing near or beside the delivery system selection list item 230 prompt. In other words, the medical chart page 405 is configured to display the chosen medical delivery system. For example, FIG. 4D is a diagram illustrating the medical chart page 405 displaying the selected medical delivery system of "VentiMask," in accordance with an exemplary embodiment of the present invention.

According to exemplary embodiments, appropriate medical data can be captured from a patient by a suitable medical analyzer or other medical data capture/analysis device or reader. In particular, blood gas analysis results can be obtained from a blood sample provided by the medical analyzer. However, such a medical analyzer can be configured to perform an analysis of the blood or any other suitable type of medical sample taken or otherwise captured from the patient. According to exemplary embodiments, the samples can comprise, for example, blood, serum, plasma, urine, saliva, cheek swab, cerebrospinal fluid, or any other suitable type of sample that can be taken from a patient. The medical data can comprise information associated with one or more of such samples (e.g., where the sample was taken from and other like information about the sample, in addition to information obtained from the sample itself). However, as discussed previously, patients can be on a medical delivery system at the time the medical data or sample is taken, and how such a medical delivery system is set up can affect the interpretation of, for example, the blood gas and other analysis results provided by the medical analyzer. According to exemplary embodiments, the medical data or sample is analyzed in accordance with the entered operation data. In other words, the operating parameters entered through the appropriate parameter page (e.g., parameter page 420 of FIG. 4C) can be used by the medical analyzer in the analysis of the patient sample to provide a better interpretation of such medical data (using suitable algorithms, rules, logic, or the like). Use of such operating parameters in the analysis of the medical data by the medical analyzer will depend on such factors as, for example, the type of medical analyzer being used, the type of analysis being performed, the type of medical delivery system the patient is on, how such medical delivery system is set up, and other like factors that those of ordinary skill in the art will recognize.

Once all or substantially all of the appropriate information is entered into the medical chart and parameter pages and the analysis performed, the results of the analysis can be displayed to the user. Referring again to FIG. 1A, the system 100 can include an analysis display module 115 in communication with at least the first user interface display module 105. The analysis display module 115 is configured to generate and display sample analysis results or other medical analysis results of the medical data analyzed in accordance with the entered operation data. The analysis display module 115 can also be configured to display the medical data or other suitable information along with the medical analysis results (e.g., blood sample analysis results or the like). In other words, the analysis display module 115 can be configured to display any appropriate sample analysis or other medical analysis results, as entry of the operation and other like data is not required for obtaining or displaying such results. However, the system 100 can be configured to require entry of such operation and other like data before displaying the analysis results, if desired.

Figure 5A:
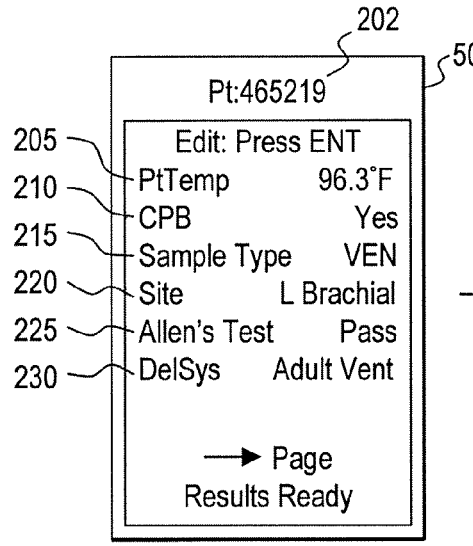
FIG. 5A is a diagram illustrating a customized medical chart page with the first five medical chart page items completed, in accordance with an exemplary embodiment of the present invention.
Figure 5B:
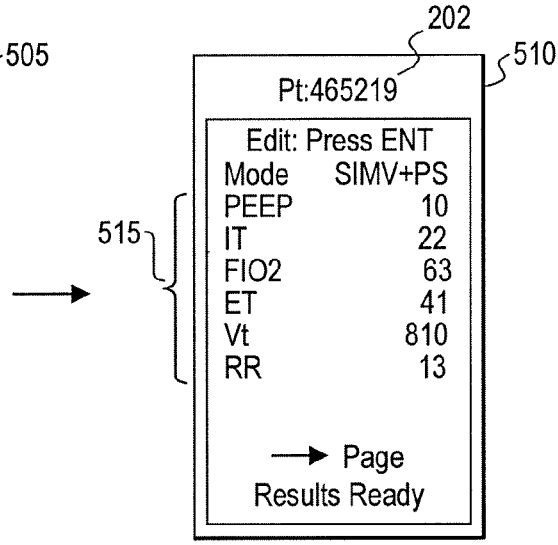
FIG. 5B is a diagram illustrating a parameter page displaying the parameter fields for entry of the operation data associated with a mode choice of the "Adult Vent" delivery system chosen from the selection list page of FIG. 4B, in accordance with an exemplary embodiment of the present invention.

For purposes of illustration and not limitation, FIG. 5A is a diagram illustrating a customized medical chart page 505 with the first six medical chart page items (data entry item 205 and selection list items 210, 215, 220, 225 and 230) of medical chart page 200 completed, in accordance with an exemplary embodiment of the present invention. As shown in FIG. 5A, an "Adult Vent" (adult ventilator) has been chosen as the medical delivery system (e.g., from the medical selection list page 410 illustrated in FIG. 4B), and such choice is displayed next to or near the delivery system selection list item 230 prompt in FIG. 5A. To enter parameter or operation data associated with the adult ventilator, FIG. 5B is a diagram illustrating a parameter page 510 displaying the parameter fields 515 for entry of the operation data associated with a mode choice (as discussed below) of the "Adult Vent" delivery system chosen from the selection list page 410 of FIG. 4B, in accordance with an exemplary embodiment of the present invention. For purposes of illustration and not limitation, operation data for an adult ventilator can include, for example, "PEEP" representing "Positive End—Expiratory Pressure," "IT" representing "Inspiratory Time," "FIO2" representing "Fractional Inspired Oxygen," "ET" representing "Expiratory Time," "Vt" representing "Tidal Volume," and "RR" representing "Respiratory Rate." As noted previously, the quantity and types of operation data displayed in the parameter page window will depend on the chosen medical delivery system.

Figure 5C:
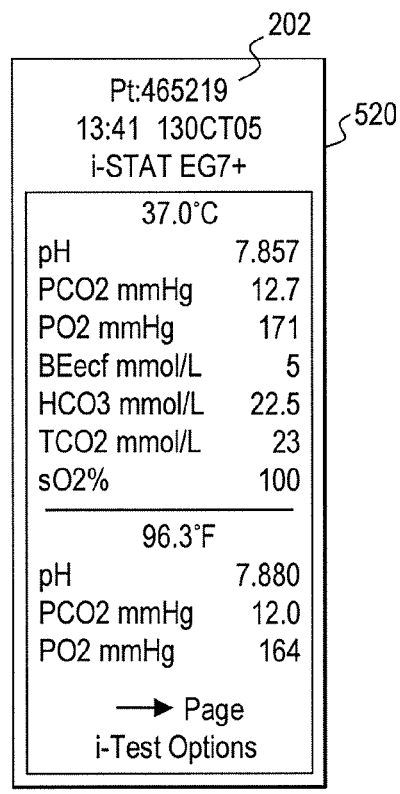
FIGS. 5C and 5D are diagrams illustrating sample analysis results that can be generated by the analysis display module in accordance with the entered operation data, in accordance with an exemplary embodiment of the present invention.
Figure 5D:
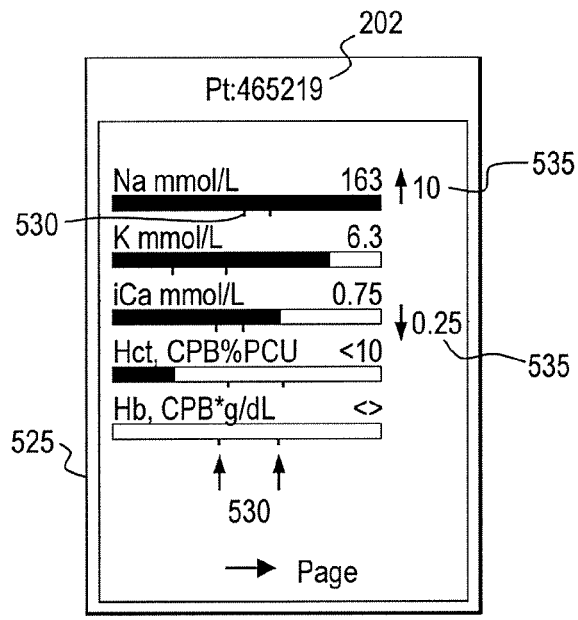

Continuing with the present illustration, after i.) the operation data is entered into the appropriate parameter fields in parameter page 510, ii.) the medical or other data is entered into the appropriate fields in the medical chart page 505, and iii.) the analysis of the medical data is performed in accordance with the operation data (e.g., by a suitable medical analyzer), the analysis display module 115 can be configured to generate a suitable display of analysis results (although, as noted previously, entry of the operation data is not required to display analysis results). For example, FIGS. 5C and 5D are diagrams illustrating sample analysis results that can be generated by the analysis display module 115 in accordance with the entered operation data, in accordance with an exemplary embodiment of the present invention. For example, FIG. 5C illustrates a first sample analysis results page 520 providing a predominantly textual display of numerical values of results associated with the sample analysis (e.g., measurements of blood pH, pCO2, pO2, and other like measurements). FIG. 5D illustrates a second sample analysis results page 525 providing a combination of graphical (e.g., bar graphs) and textual (e.g., numerical values) displays of additional results associated with the given sample analysis (e.g., measurements of blood sodium and potassium, and other like measurements). Other suitable analysis results can be generated and displayed to the user by the analysis display module 115 through one or more analysis results pages. The analysis results can be displayed or otherwise provided to the user in graphical or textual form, or any suitable combination thereof. Those of ordinary skill will recognize that other values can be calculated from blood gas results, including, but not limited to, excess "BE," bicarbonate ("HCO3"), total carbon dioxide ("TCO2") and percentage oxygen saturation ("sO2%"), as shown in FIG. 5C.

FIGS. 5A-5D also illustrate how a medical analyzer or other medical data capture/analysis device or reader can use the operating parameters to analyze the medical data or patient samples. More particularly, FIGS. 5A-5D illustrate two examples of how the blood gas values and Hct and Hb values are adjusted based on entry in the customized medical chart page 505. For example, the last three lines of FIG. 5C show the pH, PCO2 and PO2 values adjusted (through appropriate calculation) to represent the values at the patient temperature entered in FIG. 5A. Furthermore, FIG. 5D illustrates the Hct and Hb results adjusted for CPB due to the entry of "YES" in the CPB selection list items 210 in FIG. 5A.

Additionally, as shown in FIG. 5D, different "tick" marks 530 (e.g., "normal ranges"), as well as "Action Range" arrows 535, can be displayed based on the selection of, for example, the Sample Type selection list items 215 in FIG. 5A. The tick marks 530 are illustrated in FIG. 5D as small squares joined below each lateral bar (e.g., below "Na mmol/L . . . 163), and can provide an easy visual reference to the normal clinical range for the test result (e.g., numerical indicators can be displayed at or next to each tick mark 530). The Action Range arrows 535 can be comprised of arrows indicating "up"/"above" or "down"/"below" and a corresponding number that refers to the action range (e.g., for "Na" the corresponding Action Range arrow 535 indicates "up"/"above" and an action range of "10," while for "iCa" the corresponding Action Range arrow 535 indicates "down"/"below" and an action range of "0.25"). The normal and action ranges can be different, depending on the selection of, for example, the Sample Type (e.g., the definitions of normal range and action range for a Venous blood sample could be different from that of an Arterial blood sample).

According to exemplary embodiments, the system 100 can include or be in communication with the medical analyzer. For example, the system 100 can form a part of or otherwise be implemented within a suitable medical analyzer (via hardware, software, firmware or any appropriate combination thereof). Alternatively, the system 100 can be in communication with the medical analyzer using any suitable communication medium (e.g., wired, wireless, infrared, fiber optic, cable, Ethernet or the like) and communication protocol (e.g., RS-232, TCP/IP, or other suitable wired or wireless protocol). Any suitable medical analyzer or reader or other laboratory analyzer can be used that is capable of analyzing medical data captured or otherwise taken from a patient (e.g., a portable point-of-care biological fluid analysis device, such as, for example, the I-STAT1™ handheld system or other suitable medical analyzer or reader).

Referring to FIG. 1A, the first and second user interface display modules 105 and 110 and the analysis display module 115 can be configured to display information (medical chart pages, selection list pages, parameter pages, analysis results pages and any other suitable information) to a user via a display 120. The display 120 can be in communication with at least the first user interface display module 105. The display 120 can be any suitable display screen or device, monitor (e.g., CRT, LCD, plasma, ICU monitors (e.g., Philips Intelliview, GE Solar 8000M, Infusion pumps that include displays), or the like), projection device or other output device (e.g., a printer, a handheld device, such as a portable data assistant (PDA), or the like) capable of displaying information to a user. For example, according to an exemplary embodiment, if the system 100 comprises a portion of a medical analyzer, then the display 120 can comprise, for example, the display screen of the medical analyzer. Alternatively, if the system 100 is separate from the medical analyzer, then a separate display 120 can be used. Any suitable number of displays 120 can be used in addition or alternatively to any displays used by the medical analyzer. For example, the first and second user interface display modules 105 and 110 and the analysis display module 115 can be implemented in a laboratory analyzer. A PDA or other portable display device can be connected or otherwise put into communication with the laboratory analyzer for use as the display 120 for viewing generated information. Other configurations of the system 100 can be used in combination with medical analyzers and display devices.

Figure 6A:
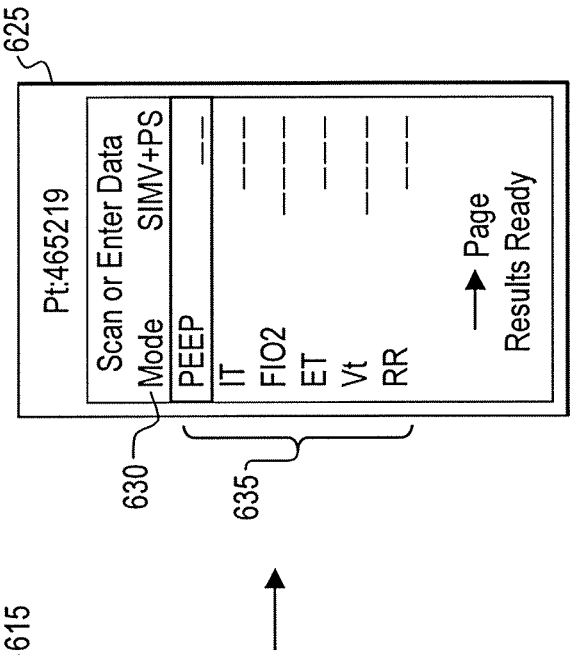
FIG. 6A is a diagram illustrating a selection list page of available delivery system choices corresponding to a delivery system selection list item from a medical chart page, in accordance with an exemplary embodiment of the present invention.

As discussed previously, the choice page displayed or otherwise presented to the user (e.g., selection list page 310 of FIG. 3B, selection list page 410 of FIG. 4B or another suitable choice page) will depend on the particular selection list item chosen from the (main) medical chart page. According to exemplary embodiments, depending on the medical delivery system chosen, a mode selection list can also be assigned to the chosen medical delivery system in order to choose the modality of that system. For purposes of illustration and not limitation, FIG. 6A is a diagram illustrating a delivery system choice or selection list page 605 of available delivery system choices 610 corresponding to a delivery system selection list item from a medical chart page (e.g., the delivery system selection list item 230 of medical chart page 200), in accordance with an exemplary embodiment of the present invention. In the present illustration, selecting the numeral "6" from the list of delivery system choices 610 can select "Adult Vent" (adult ventilator) as the desired medical delivery system. If a mode selection list has been assigned to such a selection, then the user can be presented with an appropriate mode selection page to choose the ventilator modality before being directed to the appropriate parameter entry page.

Figure 6B:
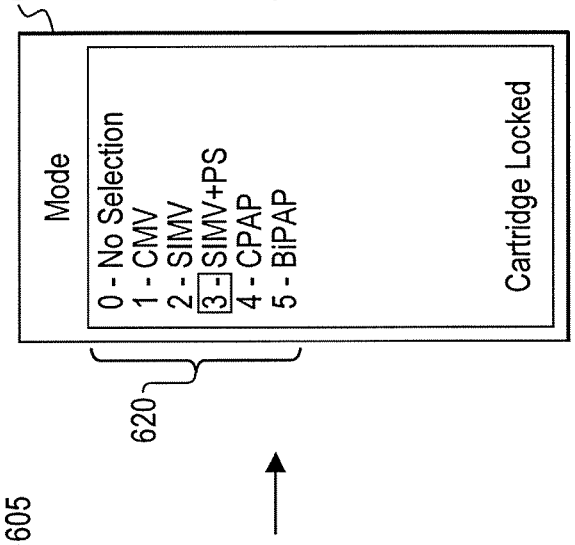
FIG. 6B is a diagram illustrating a ventilator mode selection page that appears in response to the selection of a delivery system choice from the selection list page illustrated in FIG. 6A, in accordance with an exemplary embodiment of the present invention.

For example, FIG. 6B is a diagram illustrating a ventilator mode selection page that appears in response to the selection of a delivery system choice from the selection list page illustrated in FIG. 6A, in accordance with an exemplary embodiment of the present invention. The ventilator mode selection page 615 includes a set or list of ventilator mode choices 620 corresponding to an adult ventilator. Each of the ventilator mode choices 620 can be listed or otherwise displayed in any suitable manner in the ventilator mode selection page 615. For example, each ventilator mode choice 620 can be associated with an alphanumeric designation (e.g., "0" for "No Selection," "1" for "CMV," "2" for "SIMV," "3" for "SIMV+PS," "4" for "CPAP," and "5" for "BiPAP") or other suitable designator. As will be apparent to those skilled in the respiratory care art, the abbreviations used here correspond to well-known respiratory care settings (e.g., "CMW" corresponds to "Controlled Mechanical Ventilation," "SIMV" corresponds to "Synchronized Intermittent Mandatory Ventilation," "SIMV+PS" corresponds to "SIMV+Pressure Support," "CPAP" corresponds to "Continuous Positive Airway Pressure," "BiPAP" corresponds to "Bilevel Positive Airway Pressure," and the like).

Figure 6C:
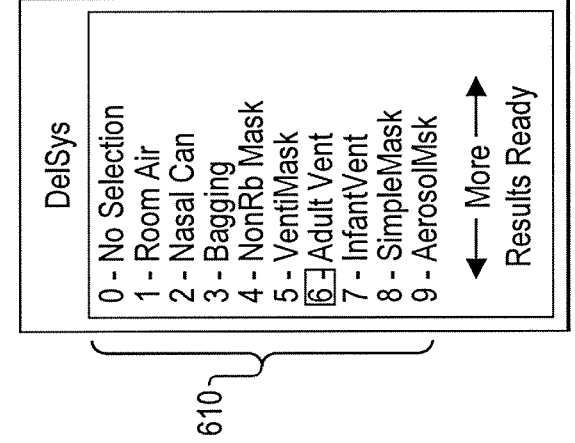
FIG. 6C is a diagram illustrating a parameter entry page for entering operation data associated with an "Adult Vent" with mode "SIMV+PS," in accordance with an exemplary embodiment of the present invention.

Accordingly, pressing the corresponding alphanumeric key of the data input device or otherwise selecting the appropriate alphanumeric designation can select the desired choice from the list of ventilator mode choices 620. Thus, the user can choose a ventilator mode from the set or list of ventilator mode choices 620 displayed in ventilator mode selection page 615. For example, selecting the numeral "3" from the list of ventilator mode choices 620 can select "SIMV+PS"" as the desired ventilator mode. Based on such a selection, the user can then be moved to a parameter entry page corresponding to the chosen medical delivery system and mode. For example, FIG. 6C is a diagram illustrating a parameter entry page 625 for entering operation data associated with an "Adult Vent" with mode "SIMV+PS," in accordance with an exemplary embodiment of the present invention. As illustrated in FIG. 6C, the chosen mode 630 (e.g., "SIMV+PS") can be displayed to the user along with the corresponding parameter fields 635. Each or any medical delivery system can include a corresponding mode selection list, and a unique parameter entry page can be assigned to each or any mode selection in the list.

It is noted that the user can edit the base and parameter page entries (e.g., to correct errors) in any suitable manner prior to the data being acknowledged or otherwise accepted for use in analysis, printing, transmitting, powering down of the medical analyzer or the like. For example, the user can move through the various pages (e.g., by making the appropriate selections) to correct any or all data as needed. The data can be acknowledged or otherwise accepted by the system 100 after the changes or modifications have been completed (e.g., after a predetermined length of time in which no input is received, by having the user select an "OK," "ACKNOWLEDGE," or "ACCEPT" button or prompt on each or any page, or the like).

Thus, referring to FIG. 1A and according to exemplary embodiments, the system 100 can include a third user interface display module 125 in communication with at least the first user interface display module 105. The third user interface display module 125 can be configured to generate and display (e.g., through display 120) a mode selection list associated with the chosen medical delivery system. The list of available choices can be displayed in any suitable manner, such as, for example, on a separate page, within the delivery system choice or selection list page (e.g., as a subpage or partition of the delivery system choice or selection list page), as a pop-up or pull-down menu of choices, or in any other appropriate manner. A mode can be chosen from the displayed mode selection list. Once the desired mode is chosen, the second user interface display module 110 can be configured to display the parameter fields in accordance with the chosen medical delivery system and mode for entry of the operation data.

As noted previously, the system 100 can be used to display any suitable information regarding patients and patient management. For example, the system 100 can include a patient data display module 130 in communication with at least the first user interface display module 105. The patient data display module 130 can be configured to display medical data, rather than analysis results, associated with each patient. For example, the patient data display module 130 can be used to display patient identity information (e.g., name and the like), medical readings taken from the patient (e.g., patient temperature and the like), physical condition of the patient, age, treatment protocol, drug therapy, patient-specified end-of-life medical intervention plan, and any other suitable information associated with the patient. Such patient data can be displayed to the user (e.g., via the display 120) either separately from or in conjunction with information displayed by other modules of the system 100. For example, the analysis display module 115 and the patient data display module 130 can work in combination (e.g., one module supplying information to the other) to display both analysis results and patient data on the same screen to the user.

Figure 1B:
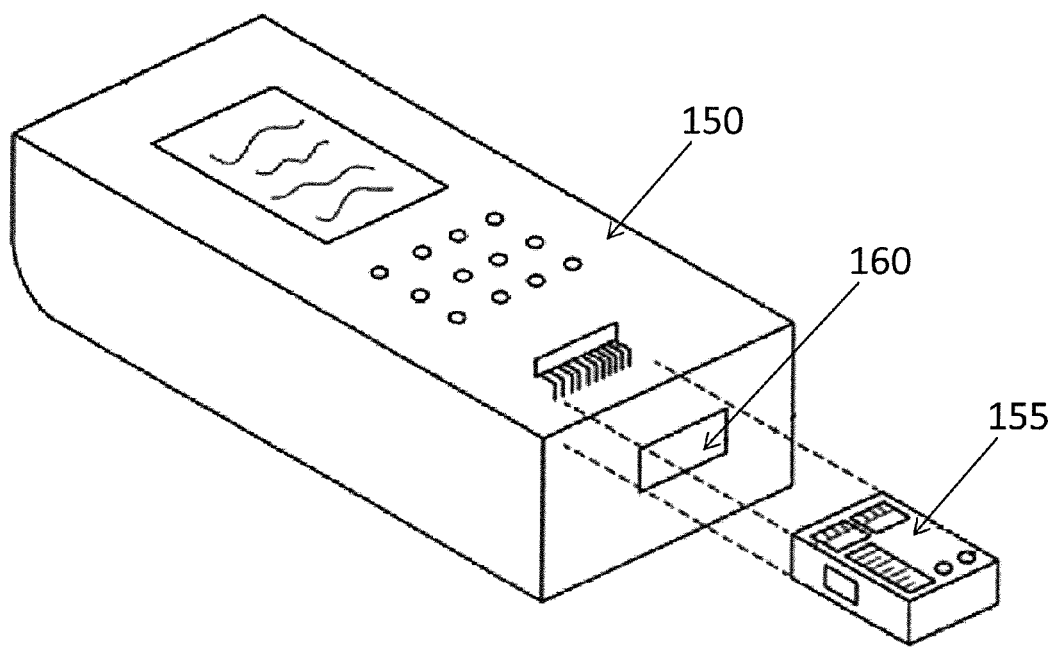

According to exemplary embodiments, the system 100 can be used in or in conjunction with a suitable medical analyzer or reader or other suitable medical data capture device. For example, the medical analyzer can be a portable blood analysis system or other portable point-ofF care biological fluid analysis device, such as, for example, the I-STAT1™ handheld system or other suitable medical analyzer. As shown in FIG. 1B, the portable medical analyzer 150 can use a disposable analyzer cartridge 155 for capturing and testing a biological fluid sample. Disposable analyzer cartridges are well-known to those of ordinary skill in the art. The disposable cartridge 155 can be mated with the medical analyzer 150 or reader using, for example, an electromechanical port 165 or other suitable connection. The disposable cartridge 155 can perform one or more electrochemical or optical analyses or other suitable analysis on, for example biological fluid, including, but not limited to, blood, plasma, saliva, serum, cheek swab, cerebrospinal fluid, urine and other like biological fluids. These biological fluids can be drawn, taken or otherwise captured from any appropriate location of a patient's body. For purposes of illustration and not limitation, the biological fluid can be blood, and the blood can be drawn from areas including, but not limited to, the right radial artery, the left radial artery, the right brachial artery, the left brachial artery, the right femoral artery, the left femoral artery, an arterial line, an umbilical line, a fingerstick, a vein, a blood capillary, a heelstick or any other suitable location. The disposable cartridge 155 can then perform a suitable analysis of such medical data or sample, including, but not limited to, pO2, pCO2, TCO2, pH, K, Na, Cl, iCa, glucose, BUN, creatinine, lactate, hematocrit, CKMB, cTnI, cTnT, BNP, NTproBNP, ACT, APTT, PT, combinations thereof, or any other suitable analysis. It is noted that one or more types of disposable cartridges can be run to obtain a complete patient data set.

The first user interface display module 105 can be configured to display a plurality of different or related medical chart pages. According to exemplary embodiments, each of the plurality of medical chart pages can be associated with a different type, make, model or the like of analyzer cartridge. Upon insertion of the cartridge into the medical analyzer, the medical analyzer can be suitably configured to detect the type of cartridge inserted into the device and generate a suitable signal indicative of the cartridge type. Any appropriate indication signal can be used that is capable of uniquely identifying each type, make, model or the like of analyzer cartridge (e.g., codes or codewords, signals of different frequency or amplitude or other suitable indicator). In a preferred embodiment, coding can be based on a connector-cartridge interaction, as described in, for example, commonly-assigned U.S. Pat. No. 4,954,087, the entire contents of which are hereby incorporated by reference herein. The indication signal can be passed or otherwise communicated to the system 100 and the first user interface display module 105. The first user interface display module 105 can be configured to display the appropriate medical chart page in accordance with the analyzer cartridge being used with the medical analyzer. Any suitable means for associating medical chart pages with analyzer cartridges can be used. For example, the system 100 can maintain a look-up table or the like (e.g., in any suitable type of computer memory or storage) that maps indication signals to analyzer cartridges and corresponding medical chart pages. Once the indication signal is received, the first user interface display module 105 can use the indication signal to look-up the corresponding analyzer cartridge and associated medical chart page from the table, and then generate and display the associated medical chart page via the display 120. Other means (e.g., appropriate algorithms, rules, or logic) for associating medical chart pages and analyzer cartridges can also be used (e.g., using suitable sorting algorithms for sorting and maintaining a correspondence between medical chart pages and analyzer cartridges).

As there can be a plurality of medical chart pages maintained by the system 100, the system 100 can include or be in communication with a medical chart page manager module 135. The medical chart page manager module 135 can be in communication with at least the first user interface display module 105. As discussed in more detail below, the medical chart page manager module 135 can be configured to manage or otherwise maintain medical chart pages and other appropriate information used by the system 100. For example, the medical chart page manager module 135 can be configured to assign medical chart pages to analyzer cartridge types. According to an exemplary embodiment, the medical chart page manager module 135 can be used to create the look-up table or other cross-referencing information that can be used by first user interface display module 105 to look-up medical chart pages assigned to analyzer cartridge types.

According to additional exemplary embodiments, the medical chart page manager module 135 can be configured to assign medical chart pages to other data used by or otherwise associated with the system 100. For example, the medical chart page manager module 135 can be configured to assign medical chart pages to operation data associated with each medical delivery system. The medical chart page manager module 135 can be used to create the look-up table or other cross-referencing information that can be used by first user interface display module 105 to look-up medical chart page(s) assigned to a chosen medical delivery system. For example, once a user selects the desired medical delivery system, the first user interface display module 105 can use the suitable look-up table or other appropriate means to look-up the medical chart page associated with the chosen medical delivery system (e.g., if a ventilator is the chosen medical delivery system, the corresponding medical chart page with appropriate ventilator fields and prompts can be retrieved for display of such information). The medical chart page can then be displayed by the first user interface display module 105 via display 120. According to an alternative exemplary embodiment, such medical chart page assignment information can reside in the medical chart page manager module 135. However, in run-time/real-time (or near real-time), the first user interface display module 105 can query the medical chart page manager module 135 (e.g., via a wired or wireless connection) for the appropriate look-up and assignment information. In other words, such look-up tables can reside in either the medical chart page manager module 135 and/or any or all of the other modules of the system 100 to allow each module to query these tables or other like information from a central store or repository (e.g., the medical chart page manager module 135) or from a local repository or storage (e.g., a memory or other computer storage medium associated with the given module).

Additionally or alternatively, the medical chart page manager module 135 can be configured to assign medical chart pages to medical data associated with each patient. The medical chart page manager module 135 can be used to create the look-up table or other cross referencing information that can be used by first user interface display module 105 to look-up medical chart page(s) assigned to the medical or patient data associated with each patient. For example, depending on the medical data captured from a patient (e.g., blood samples or the like), the first user interface display module 105 can use the suitable look-up table or other appropriate means to look-up the medical chart page associated with the given medical data (e.g., a medical chart page for exhibiting blood sample information). The medical chart page can then be displayed by the first user interface display module 105 via display 120. Those of ordinary skill will recognize that medical chart pages can be assigned to still other data used by or otherwise associated with the system 100, as the previously-described exemplary embodiments are merely illustrative and not exhaustive. For purposes of illustration and not limitation, the medical chart page manager 135 can be configured to assign medical chart pages to a disease state(s). For example, a medical delivery or treatment system according to exemplary embodiments of the present invention can comprise a chemotherapy plan or regiment, and such a system can have a different set of parameters than a treatment system for renal failure or cardiac distress.

The plurality of medical chart pages can be maintained by the system 100 in any suitable manner. For example, individual medical chart pages can be pre-stored in the system 100 for later retrieval and display, with a different medical chart page for each type of information (e.g., analyzer cartridge type, operation data, medical data, and the like) that can be viewed by users. Alternatively, more general "template" medical chart pages can be maintained by the system 100, with the specifics of each medical chart page populated and rendered depending on the information to be viewed by the user (e.g., a template analyzer cartridge type page, a template operation data page, and a template medical data page). For example, referring to FIG. 1A, the system 100 can include a database or storage module 140 in communication with at least the first user interface display module 105. The storage module 140 can be any suitable type of computer memory or storage medium that can be configured to store any suitable information used and/or maintained by the system 100, including, for example, operation data, patient data, medical data, medical chart pages, analysis results for each patient (e.g., blood sample analysis results or the like), or any other appropriate information for patient management. Each of the modules of the system 100 can retrieve or otherwise access such information from the storage module 140, although any suitable number of storage modules 140 can be used with the system 100 (e.g., each or any module of the system 100 can be associated with its own storage module 140). Additionally, one or more storage modules 140 can be located remotely from the system 100. Such remote storage can be used to store or otherwise collect information uploaded from one or more systems 100 (e.g., any or all systems 100 being used within a location, such as a location within a hospital, any or all systems 100 being used across multiples locations, such as all locations within a hospital, and the like).

According to exemplary embodiments, the medical chart pages can be customized to suit the user's needs, the equipment being used, the patient information to be managed, and other like factors. For example, the medical chart page can be customized in accordance with the location of use of the system 100. The location can comprise, for example, a location within a hospital, such as an intensive care unit, a critical care unit, a general ward, an operating room, an emergency department or other suitable location within the hospital or other area where medical services or therapy are administered, such as, for example, a physician's office or an ambulance. As noted above, the medical chart pages can be customized in accordance with the type, make, model or the like of analyzer cartridge being used. Other such customizations of the medical chart pages can also be performed to suit the needs of the users, depending on the type and content of the information to be displayed.

As discussed previously, the medical chart page manager module 135 can be used to customize the medical chart pages. According to an exemplary embodiment, the medical chart page manager module 135 can be implemented and run in any suitable graphical, windowed operating system environment, such as, for example, the Microsoft WINDOWS™ family of windowed operating systems that run on personal computers. The medical chart page manager module 135 can be configured to generate various windows or other graphical and/or textual layouts for modifying different aspects of the medical chart pages. The medical chart page manager module 135 can be in communication with the system 100 to download or otherwise transfer the medical chart pages (e.g., into storage module 140) and other appropriate information for later use by one or more of the modules of system 100. For example, the medical chart page manager module 135 can be configured to download such information to any or all of the medical analyzers or other point-of-care devices at a given location or across locations. Such downloading can be performed using any suitable type of wired or wireless network or other computer connection (e.g., LAN, WAN, infrared, radio frequency, optical, cable, and the like).

Figure 7:
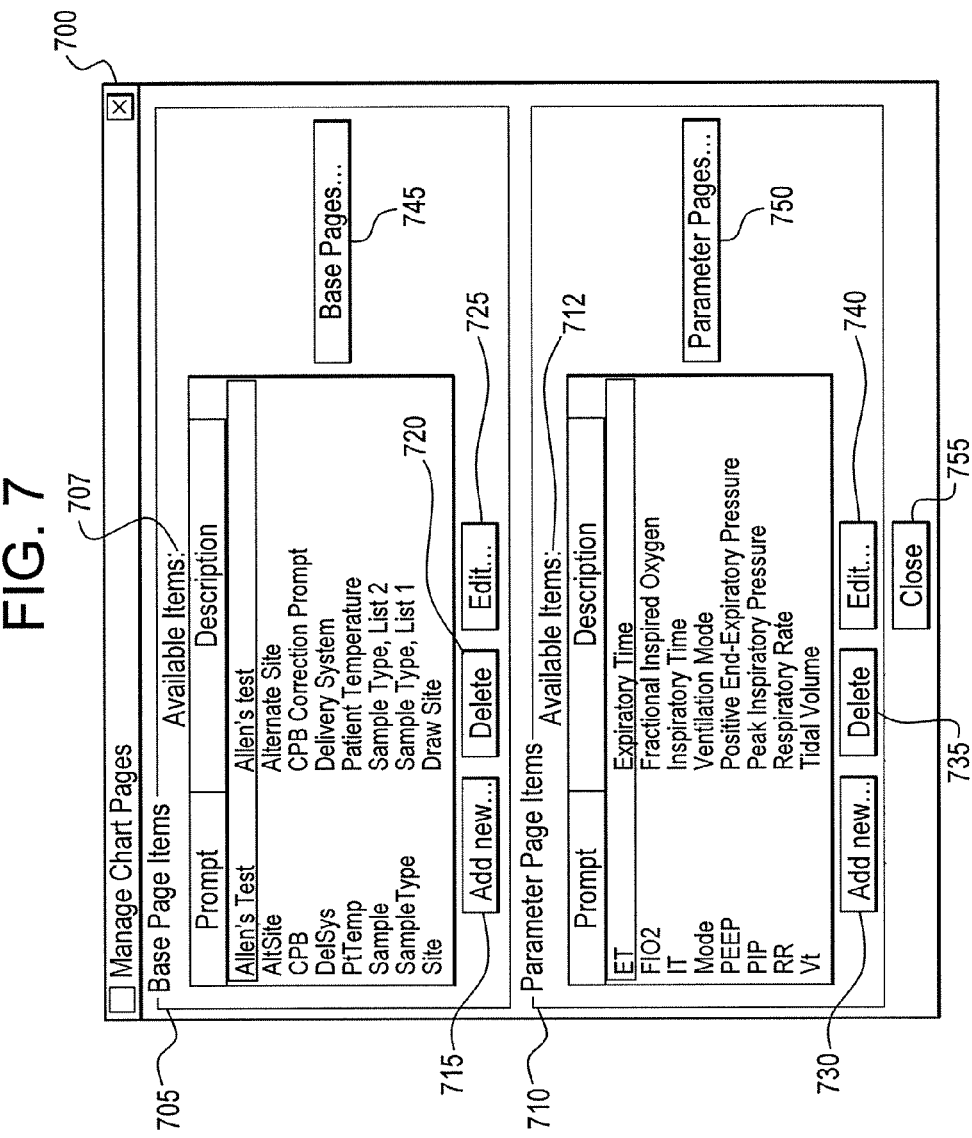
FIG. 7 is a diagram illustrating a manage chart page window for creating custom medical chart pages, in accordance with an exemplary embodiment of the present invention.

FIG. 7 is a diagram illustrating a manage chart page window 700 for creating custom medical chart pages, in accordance with an exemplary embodiment of the present invention. A custom chart page can be comprised of a base page and associated parameter pages. The base page is the initial medical chart page that appears on the display 120, for example, during an analyzer cartridge run. For example, medical chart page 200 of FIG. 2 is an example of a base page. The parameter pages are comprised of items used to record additional parameters depending on the selected medical delivery system or medical delivery system/mode, as discussed previously. For example, parameter pages 420 (of FIG. 4C), 510 (of FIG. 5B) and 625 (of FIG. 6C) are examples of parameters pages. The medical chart pages can be customized via the manage chart page window 700 that can be accessed from, for example, the medical chart page manager module 135. For example, if the medical chart page manager module 135 is being run in a WINDOWS™ graphical operating system environment or the like, the user can access the manage chart page window 700 by appropriately opening or otherwise accessing the medical chart page manager module 135, selecting "Tools" from the menu bar, and "Manage Chart Pages" from the corresponding pull-down menu.

As illustrated in FIG. 7, the manage chart page window 700 can be separated into two sections: the base page items section 705 and the parameter page items section 710. The base page items section 705 can display a list of available items 707 that can be included on any base page. For example, the items "PtTemp," "CPB," "Sample Type," "Site," "Allen's Test," and "DelSys" from the list of available items 707 in the base page items section 705 could be used to create and populate the medical chart page 200 illustrated in FIG. 2. The parameter page items section 710 can show a list of available items 712 that can be included on any parameter page. For example, the items "IT," "RR," "Vt," and "FIO2" from the list of available items 712 in the parameter page items section 710 could be used to create and populate the parameter page 420 illustrated in FIG. 4C. Each section can provide the ability to add new, delete and edit data entry and selection list items (e.g., via add new buttons 715 and 730, delete buttons 720 and 735, and edit buttons 725 and 740, located respectively in the base and parameter page items section 705 and 710). In the base page items section 705, the base pages button 745 can be configured to display a window used to build base pages using the base page items. In the parameter page items section 710, the parameter pages button 750 can be configured to display a window used to build parameter pages using the parameter page items.

Figure 8:
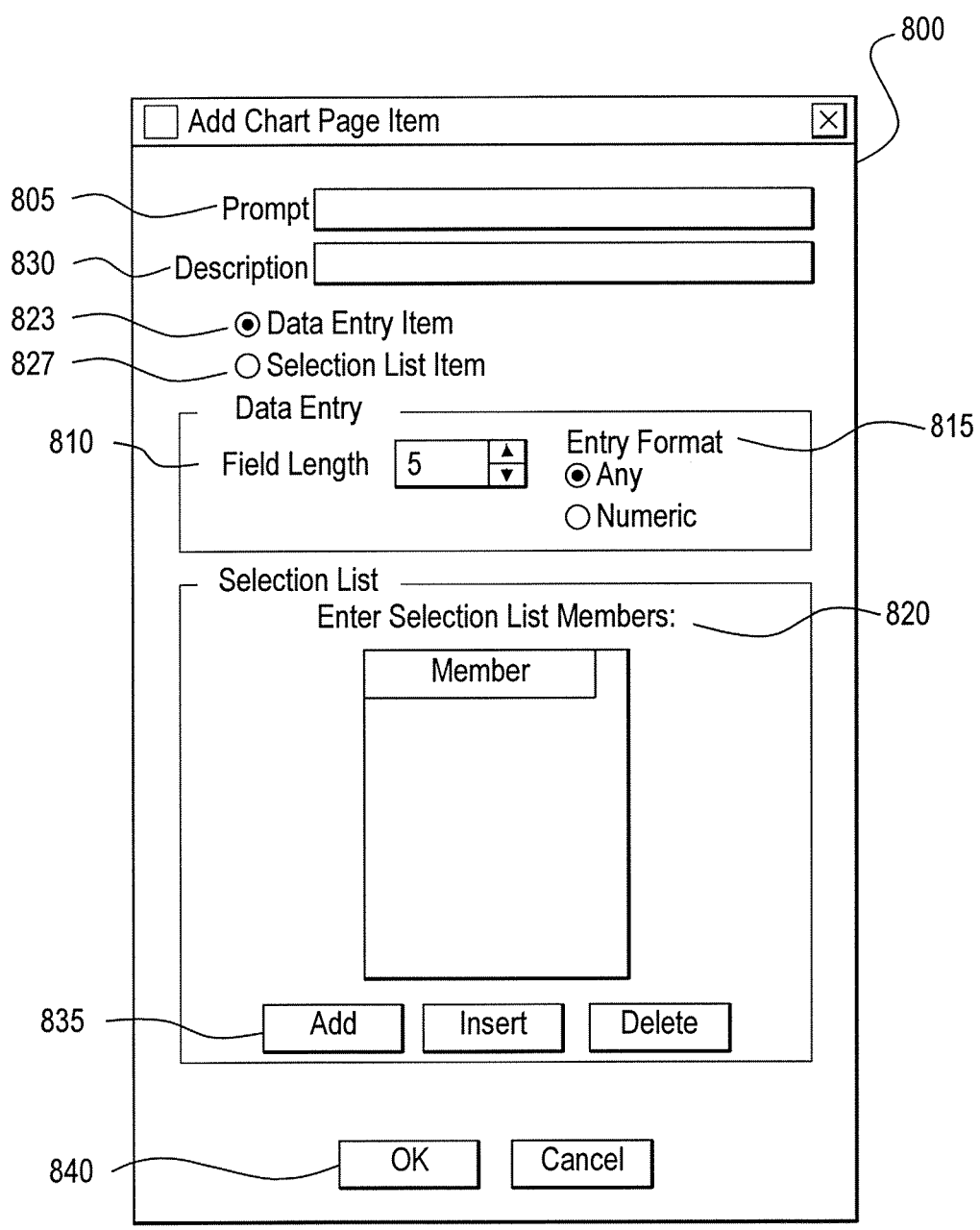
FIG. 8 is a diagram illustrating an add chart page item window, in accordance with an exemplary embodiment of the present invention.

According to an exemplary embodiment, to create new base pages and parameter page items, an add chart page item window can be used. FIG. 8 is a diagram illustrating an add chart page item window 800, in accordance with an exemplary embodiment of the present invention. The add chart page item window 800 can provide the ability to create data entry and selection list items for both base and parameter pages. According to an exemplary embodiment, data entry items can include a prompt field 805 (e.g., for entering a suitable alphanumeric prompt for the item), a field length 810 (e.g., a value indicating the length of the field), and an entry format 815 (e.g., "any" representing alphanumeric format, or "numeric" representing numeric format only). Selection list items can include the prompt field 805 and a list of suitable members 820 from which to choose. Two radio buttons—data entry item radio button 823 and selection list item radio button 827—can be used to select between either data entry items or selection list items for creation.

To create new base page items from the manage chart page window 700 of FIG. 7, the add new button 715 can be selected in the base page items section 705. Alternatively, to create new parameter page items from the manage chart page window 700 of FIG. 7, the add new button 730 can be selected in the parameter page items section 710 of the manage chart page window 700. Selecting either button can cause the add chart page item window 800 to be displayed. For the prompt field 805, the user can enter the prompt for the new item as it should appear on the display 120. Optionally, the user can enter a description 830 of the prompt. If creating a data entry item, the user can select the data entry item radio button 823. The appropriate field length can be chosen from the field length 810. The entry format 815 can be chosen by selecting either the "Any" radio button or the "Numeric" radio button under the entry format 815. Such a feature can allow for entry "filters" to be applied to the entered data to force an entry into a predetermined format (e.g., a fixed number of decimal places, such as "x.xx," integer only numbers, alpha-only entries, and the like). If creating a selection list item, the user can select the selection list item radio button 827. The user can then select the add button 835 under the members 820 section. The user can then specify the selection list member as it will appear on the display 120. The user can repeatedly select the add button 835 and enter a selection list member until all list members 820 have been entered. Once completed, the user can select the okay button 840 to accept the item.

Figure 9:
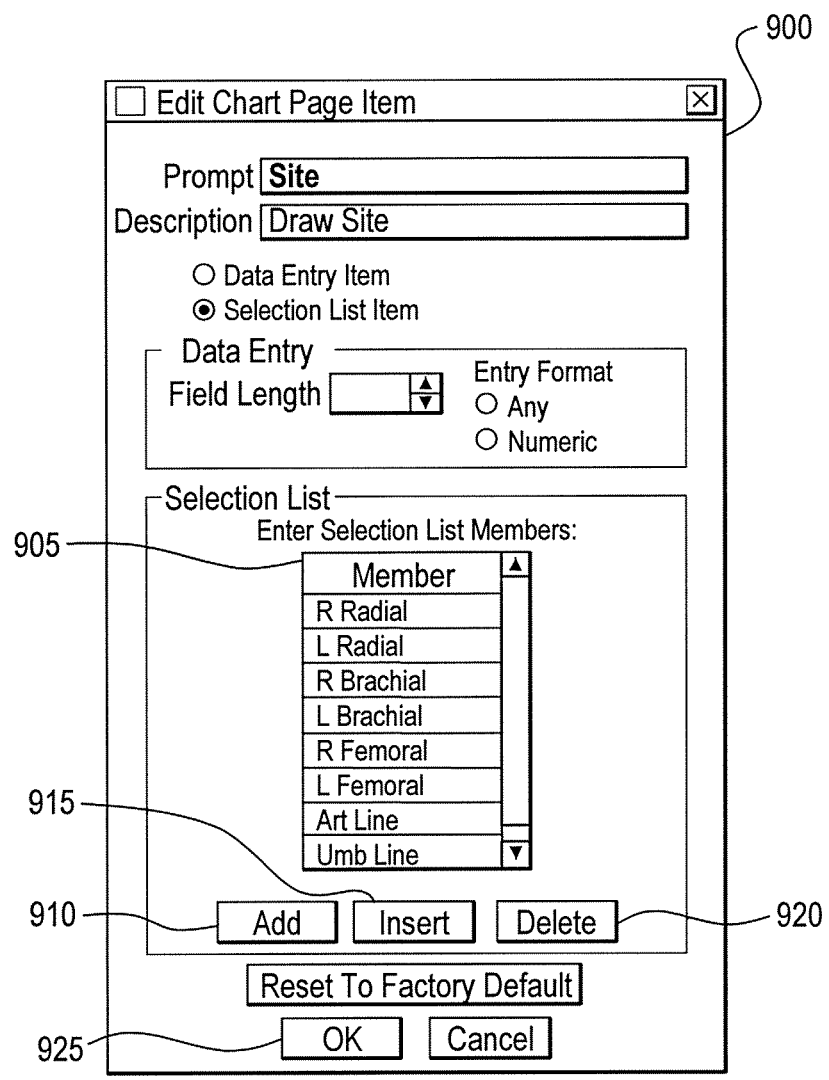
FIG. 9 is a diagram illustrating an edit chart page item window, in accordance with an exemplary embodiment of the present invention.

According to an exemplary embodiment, to edit base or parameter page items, an edit chart page item window can be used. FIG. 9 is a diagram illustrating an edit chart page item window 900, in accordance with an exemplary embodiment of the present invention. The edit chart page item window 900 can provide the ability to edit existing data entry and selection list items for both base and parameter pages. To edit base page items, the base page item to be edited can be highlighted or otherwise selected from the base page items section 705 of the manage chart page window 700 of FIG. 7, and the edit button 725 can be selected. Alternatively, to edit new parameter page items, the parameter page item to be edited can be highlighted or otherwise selection from the parameter page items section 710 of the manage chart page window 700, and the edit button 740 can be selected. Selecting either button can cause the edit chart page item window 900 to be displayed, with non-editable items being grayed out or otherwise de-selected in the member list 905. To add a new selection list member to the bottom of the member list 905, the user can click or select the add button 910. The user can then enter the name of the new list member, and click the add button 910 again. To insert a new selection list member in the middle of the member list 905, the user can highlight or otherwise select the member item directly below where the user wants the new item to appear. The user can then click or select the insert button 915, causing a blank entry to appear immediately before the highlighted line. The user can then enter the name of the new list member, and, for example, click anywhere else in the member list 905 to accept the new entry. To delete a selection list member, the user can highlight or otherwise select the list member to be deleted, and the click the delete button 920. When editing is complete, the user can select the okay button 925 to accept all changes.

To delete base or parameter page items, the user can use the delete buttons in the manage chart page window 700 of FIG. 7. To delete a base page item, the user can highlight or otherwise select a base page item from the base page items section 705, and then press or otherwise click the delete button 720. To delete a parameter page item, the user can highlight or otherwise select a parameter page item from the parameter page items section 710, and then press or otherwise click the delete button 735. Once all desired items have been deleted, the user can click the close button 755 to exit.

Figure 10:
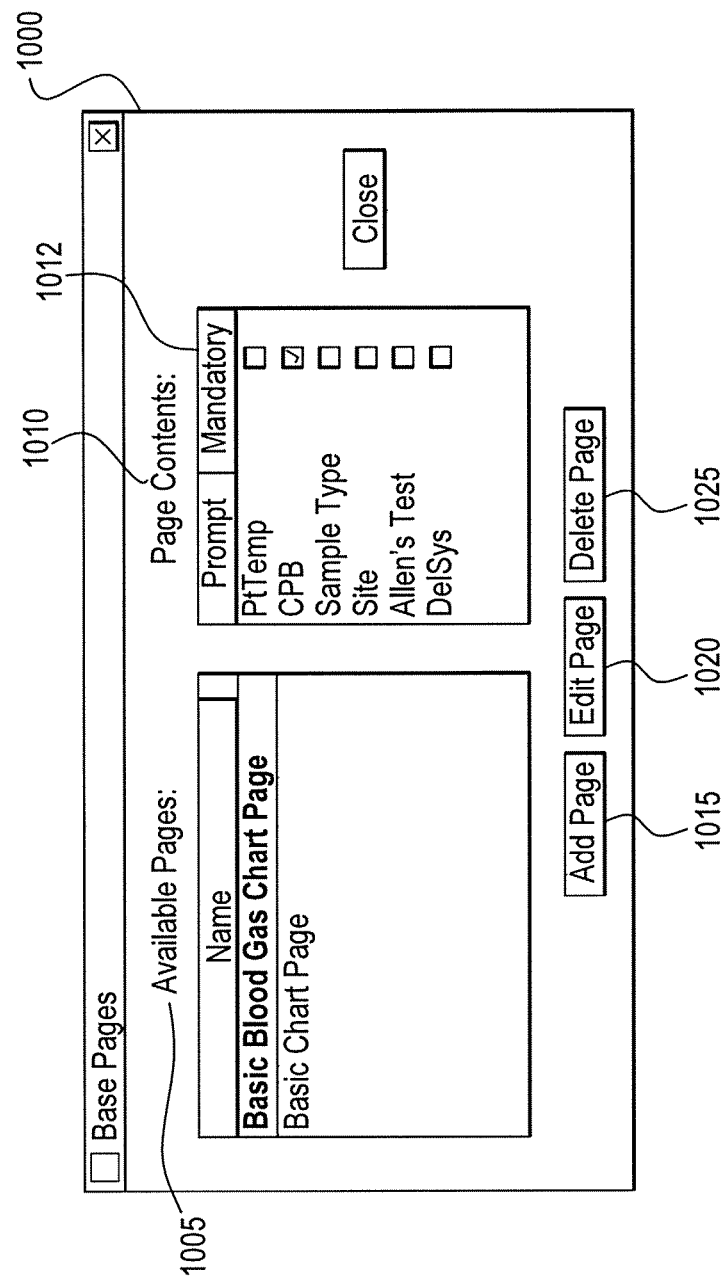
FIG. 10 is diagram illustrating a base pages window, in accordance with an exemplary embodiment of the present invention.

The manage chart page window 700 can also be used to build base pages containing the base page items created via the manage chart page window 700. A base pages window can be accessed by the user by clicking or otherwise selecting the base pages button 745 in the base page items section 705. FIG. 10 is diagram illustrating a base pages window 1000, in accordance with an exemplary embodiment of the present invention. The base pages window 1000 can provide the ability to create base pages as they will appear on the display 120. According to an exemplary embodiment, each base page can include up to ten unique base page items in any order, although each base page can include any appropriate number of base page items. The base pages window 1000 can display a list of the available pages 1005 and the page contents 1010 of the highlighted page. Any item listed in the page contents 1010 section can be deemed as a mandatory item 1012 by checking the corresponding check box. For example, in the illustration of FIG. 10, the item "CPB" has been checked as "mandatory." The base pages window 1000 can also provide the ability to add, edit and delete base pages via add page button 1015, edit page button 1020, and delete page button 1025, respectively. According to an exemplary embodiment, pre-defined base pages can be provided to the user, and be edited or deleted as needed. For example, Table 1 lists two pre-defined base pages and the contents of each of those (pre-defined) base pages:

TABLE 1

Examples of two pre-defined base pages and contents of each.

| BASE PAGE NAME | BASE PAGE CONTENTS |
|---|---|
| Basic Blood Gas Chart Page | PtTemp |
| | CPB (Mandatory) |
| | Sample Type |
| | Site |
| | Allen's Test |
| | DelSys |
| Basic Chart Page | Sample Type |
| | CPB (Mandatory) |

Figure 11:
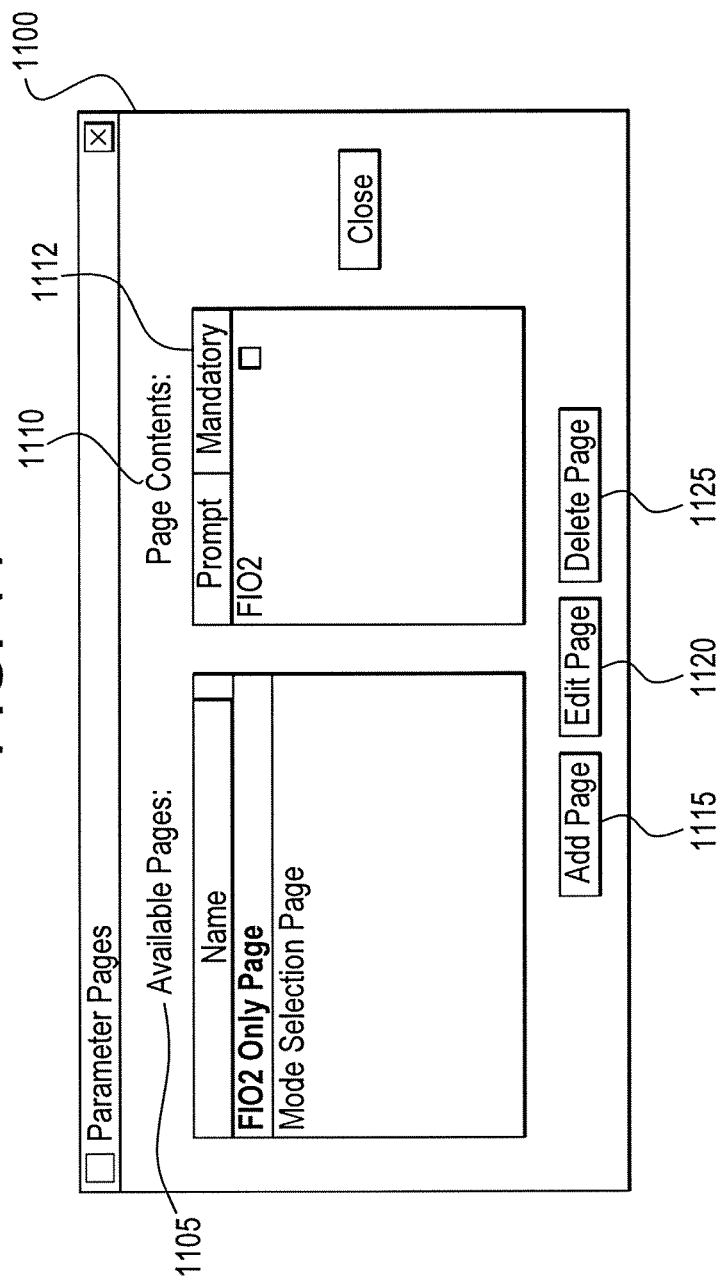
FIG. 11 is diagram illustrating a parameter pages window, in accordance with an exemplary embodiment of the present invention.

The manage chart page window 700 can also be used to build parameter pages containing the parameter page items created via the manage chart page window 700. Parameter pages can be used to enter additional and/or alternative operation data or other parameters depending on the selection medical delivery system or mode. For example, unique parameter pages can be assigned to specific selection list members in the "DelSys" base page item, as well as the mode parameter page item illustrated in FIG. 7. A parameter pages window can be accessed by the user by clicking or otherwise selecting the parameter pages button 750 in the parameter page items section 710. FIG. 11 is diagram illustrating a parameter pages window 1100, in accordance with an exemplary embodiment of the present invention. The parameter pages window 1100 can provide the ability to create parameter pages as they will appear on the display 120. According to an exemplary embodiment, each parameter page can include up to nine unique parameter page items in any order, although each parameter page can include any appropriate number of parameter page items. The parameter pages window 1100 can display a list of the available pages 1105 and the page contents 1110 of the highlighted page. Any item listed in the page contents 1110 section can be deemed as a mandatory item 1112 by checking the corresponding check box. The parameter pages window 1100 can also provide the ability to add, edit and delete parameter pages via add page button 1115, edit page button 1120, and delete page button 1125, respectively. According to an exemplary embodiment, pre-defined parameter pages can be provided to the user, and be edited or deleted as needed. For example, Table 2 lists two pre-defined parameter pages and the contents of each of those (pre-defined) parameter pages:

TABLE 2

Examples of two pre-defined parameter pages and contents of each.

| PARAMETER PAGE NAME | PARAMETER PAGE CONTENTS |
|---|---|
| FIO2 Only Page | FIO2 |
| Mode Selection Page | Mode |

According to an exemplary embodiment, a parameter page containing the mode selection list item cannot contain any additional items, although any suitable number and types of items can be included in such a page.

Figure 12:
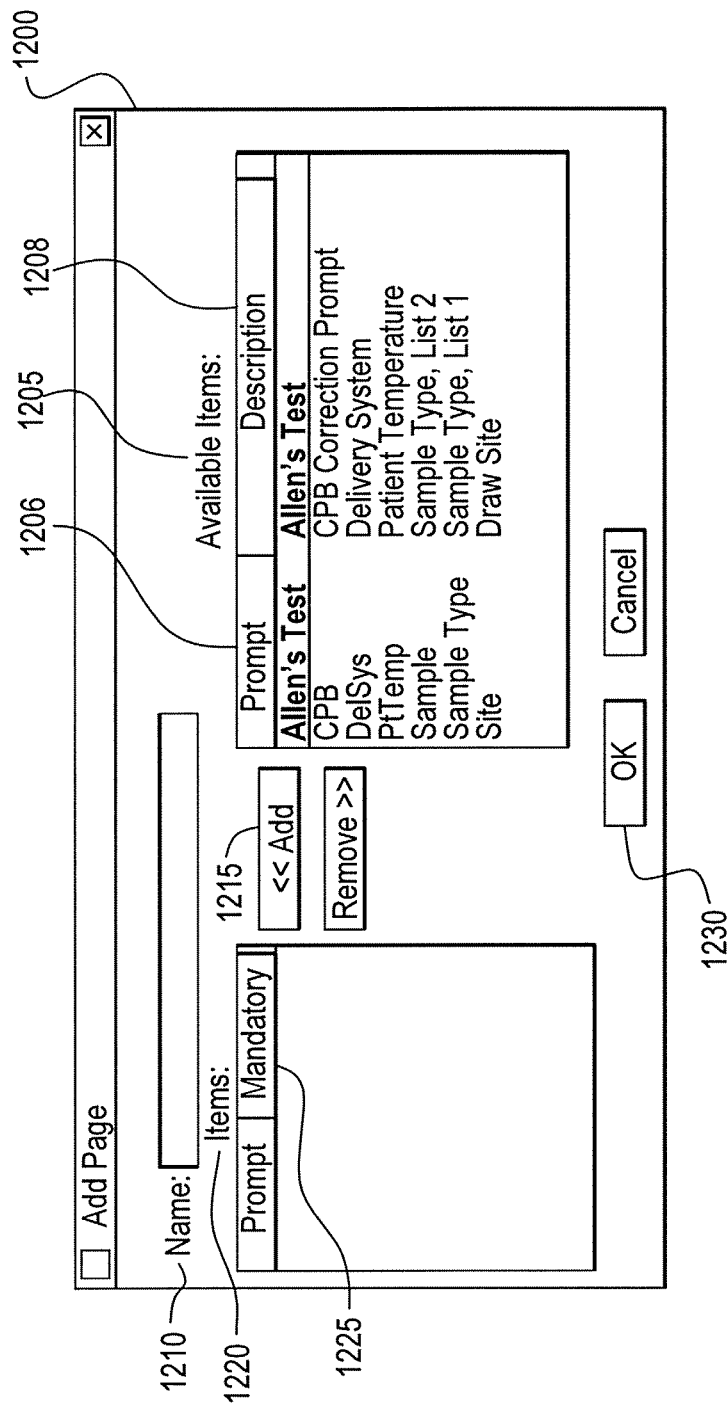
FIG. 12 is a diagram illustrating an add page window, in accordance with an exemplary embodiment of the present invention.

The manage chart page window 700 can also be used to create new base pages and parameter pages via the base pages window 1000 or the parameter pages window 1100, respectively. An add page window can provide the ability to create base and parameter pages. FIG. 12 is a diagram illustrating an add page window 1200, in accordance with an exemplary embodiment of the present invention. The add page window 1200 can be accessed by clicking the add page button 1015 from the base pages window 1000 or the add page button 1115 from the parameter pages window 1100. The add page window 1200 can provide a list of available items 1205 (including prompt field 1206 and corresponding description field 1208 for each available item) that can be added to the page being defined. In the add page window 1200, a descriptive name 1210 can be entered for the new base or parameter page. Under the available items 1205, the first item to be included in the new base or parameter page can be highlighted or otherwise selected and the add button 1215 can be clicked. Such an action will move the first item to the items section 1220. If users are required to enter the parameter, then the mandatory field 1225 can be selected by checking the appropriate check box. Additional items can be added to the items section 1220 by repeating the steps of selecting the desired item from the available items 1205 and clicking the add button 1215. Once finished, the okay button 1230 can be clicked. The new base or parameter page will then appear in the list of available pages 1005 in the base pages window 1000 or the list of available pages 1105 in the parameter pages window 1100, depending on whether a base page or parameter page was added.

Figure 13:
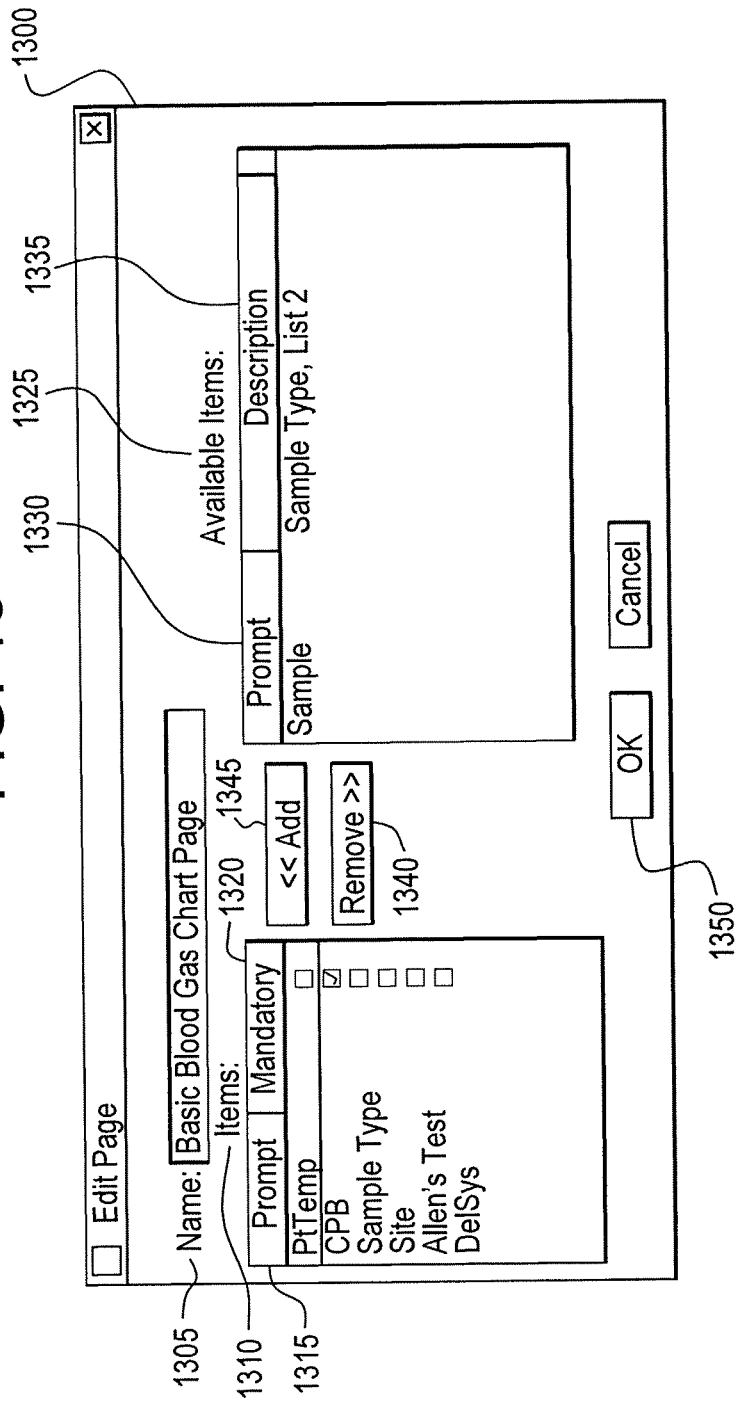
FIG. 13 is a diagram illustrating an edit page window, in accordance with an exemplary embodiment of the present invention.

Base or parameter pages can also be edited via the base pages window 1000 or the parameter pages window 1100, respectively. An edit page window can provide the ability to add and remove items from existing base and parameter pages. FIG. 13 is a diagram illustrating an edit page window 1300, in accordance with an exemplary embodiment of the present invention. The edit page window 1300 can be accessed by clicking the edit page button 1020 from the base pages window 1000 or the edit page button 1120 from the parameter pages window 1100. In the edit page window 1300, the descriptive name 1305 of the page being edited can be displayed. The edit page window 1300 can provide a list of items 1305 that currently populate the page being edited (including a prompt field 1315 and a designation (e.g., a check box) of whether the item is mandatory (e.g., via a mandatory field 1320)). Available items 1325 (including prompt field 1330 and corresponding description field 1335 for each available item) can also be displayed in the edit page window 1300 that can be added to the page being edited. To remove an item from the base or parameter page, the desired item from the list of items 1310 can be highlighted or otherwise selected, and then the remove button 1340 can be clicked (causing the item to be moved back to the list of available items 1325). To add a new item to the base or parameter page, the desired item from the list of available items 1325 can be highlighted or otherwise selected, and then the add button 1345 can be clicked (causing the item to be moved to the list of items 1310). Once moved to the list of items 1310, the check box in the mandatory field 1320 can be selected or otherwise checked if users are required to enter that parameter. Once finished, the okay button 1350 can be clicked.

According to an exemplary embodiment, the medical chart page manager module 135 (or other appropriate module) can include suitable "rules of construction" or other like rules or logic to prevent users from creating nonsensical, illogical or otherwise erroneous or unsuitable page setups, or to "force" or require users to create certain setups (e.g., add particular parameters) within a page. For purposes of illustration and not limitation, if a flow-mask ventilator is selected, the medical chart page manager module 135 could disallow or otherwise prevent the placement of a parameter of "Inspiration Time" or "Expiration Time," as such parameters are unusable or unsuitable for a mask that is set only for flow rate delivery. Alternatively, if a medical delivery system of "Insulin Pump" is selected, the medical chart page manager module 135 could force or otherwise require the user to add the parameter of, for example, "Injection Size."

Figure 14:
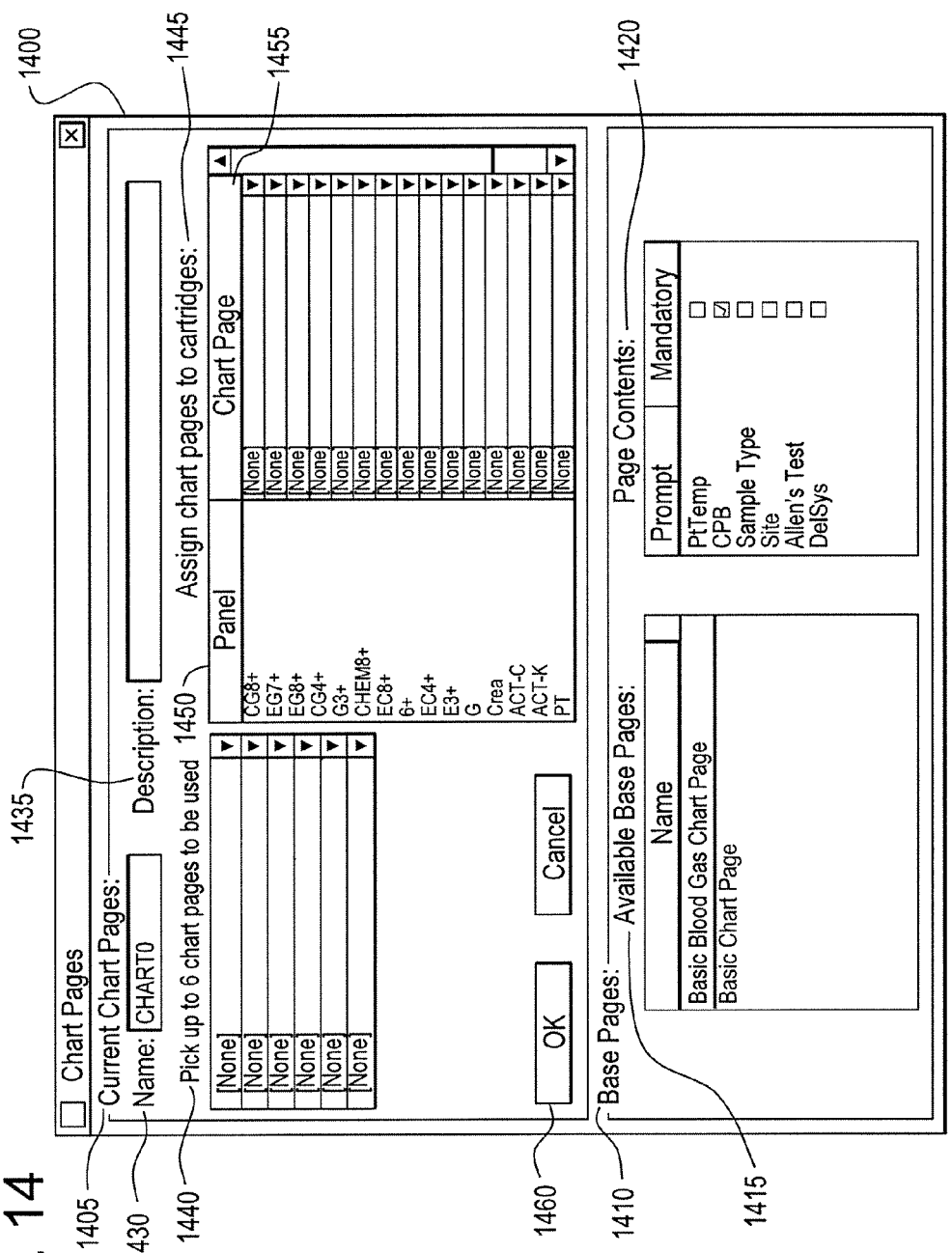
FIG. 14 is a diagram illustrating a chart pages window, in accordance with an exemplary embodiment of the present invention.

As discussed previously, the medical chart page manager module 135 can be configured to assign medical chart pages to analyzer cartridge types, operation data, patient medical data, or other like information. For example, once all medical chart pages have been created, a chart page window can be used to assign medical chart pages to, for example, individual analyzer cartridge types. FIG. 14 is a diagram illustrating a chart pages window 1400, in accordance with an exemplary embodiment of the present invention. The chart pages window 1400 can be accessed from, for example, the medical chart page manager module 135. For example, if the medical chart page manager module 135 is being run in a WINDOWS™ graphical operating system environment or the like, the user can access the chart pages window 1400 by appropriately opening or otherwise accessing the medical chart page manager module 135 and selecting "Chart Page" from under the desired customization profile.

The chart pages window 1400 can be comprised of two sections: a current pages section 1405 and a base pages section 1410. The base pages section 1410 can include a list of available base pages 1415 and a listing of the page contents 1420 that can be displayed for the selected base page. The current pages section 1405 can include the name 1430 of the current set of chart pages, and a field for a description 1435 of the set of selected chart pages. To assign chart pages to, for example, individual cartridge types, the description 1435 can be entered for the set of selected chart pages, if desired. Under the chart selection section 1440 (having a title such as, for example, "Pick up to 6 chart pages to be used"), drop down lists can be used to select the chart pages for the desired location in which the system 100 is to be used. According to an exemplary embodiment, up to six of the available base pages can be used in each location, although any suitable number of base pages can be used in each location. Under the chart assignment section 1445 (having a title such as, for example, "Assign chart pages to cartridges"), drop down lists can be used to assign specific chart pages to the cartridge(s) used in the given location. If "[NONE]" is selected, no chart page will be assigned to that cartridge type. The chart assignment section 1445 includes a panel portion 1450 that is configured to list the cartridge types, and a chart pages portion 1455 to assign the chart pages to the cartridge type. Once finished, the okay button 1460 can be clicked. It is noted that similar chart pages windows can be used for assigning chart pages to operation data, patient medical data, or other like information.

Each of modules of the system 100, including first user interface display module 105, second user interface display module 110, analysis display module 115, third user interface display module 125, patient data display module 130, medical chart page manager module 135, or any combination thereof, can be comprised of any suitable type of electrical or electronic component or device that is capable of performing the functions associated with the respective element. According to such an exemplary embodiment, each component or device can be in communication with another component or device using any appropriate type of electrical connection that is capable of carrying (e.g., electrical) information. Alternatively, each of the modules of the system 100 can be comprised of any combination of hardware, firmware and software that is capable of performing the functions associated with the respective module.

Alternatively, the system 100 can be comprised of one or more microprocessors and associated memory(ies) that store the steps of a computer program to perform the functions of any or all of the modules of the system 100. The microprocessor can be any suitable type of processor, such as, for example, any type of general purpose microprocessor or microcontroller, a digital signal processing (DSP) processor, an application-specific integrated circuit (ASIC), a programmable read-only memory (PROM), an erasable programmable read-only memory (EPROM), an electrically-erasable programmable read-only memory (EEPROM), a computer-readable medium, or the like. The memory can be any suitable type of computer memory or any other type of electronic storage medium, such as, for example, read-only memory (ROM), random access memory (RAM), cache memory, compact disc read-only memory (CDROM), electro-optical memory, magneto-optical memory, or the like. As will be appreciated based on the foregoing description, the memory can be programmed using conventional techniques known to those having ordinary skill in the art of computer programming. For example, the actual source code or object code of the computer program can be stored in the memory.

Figure 15:
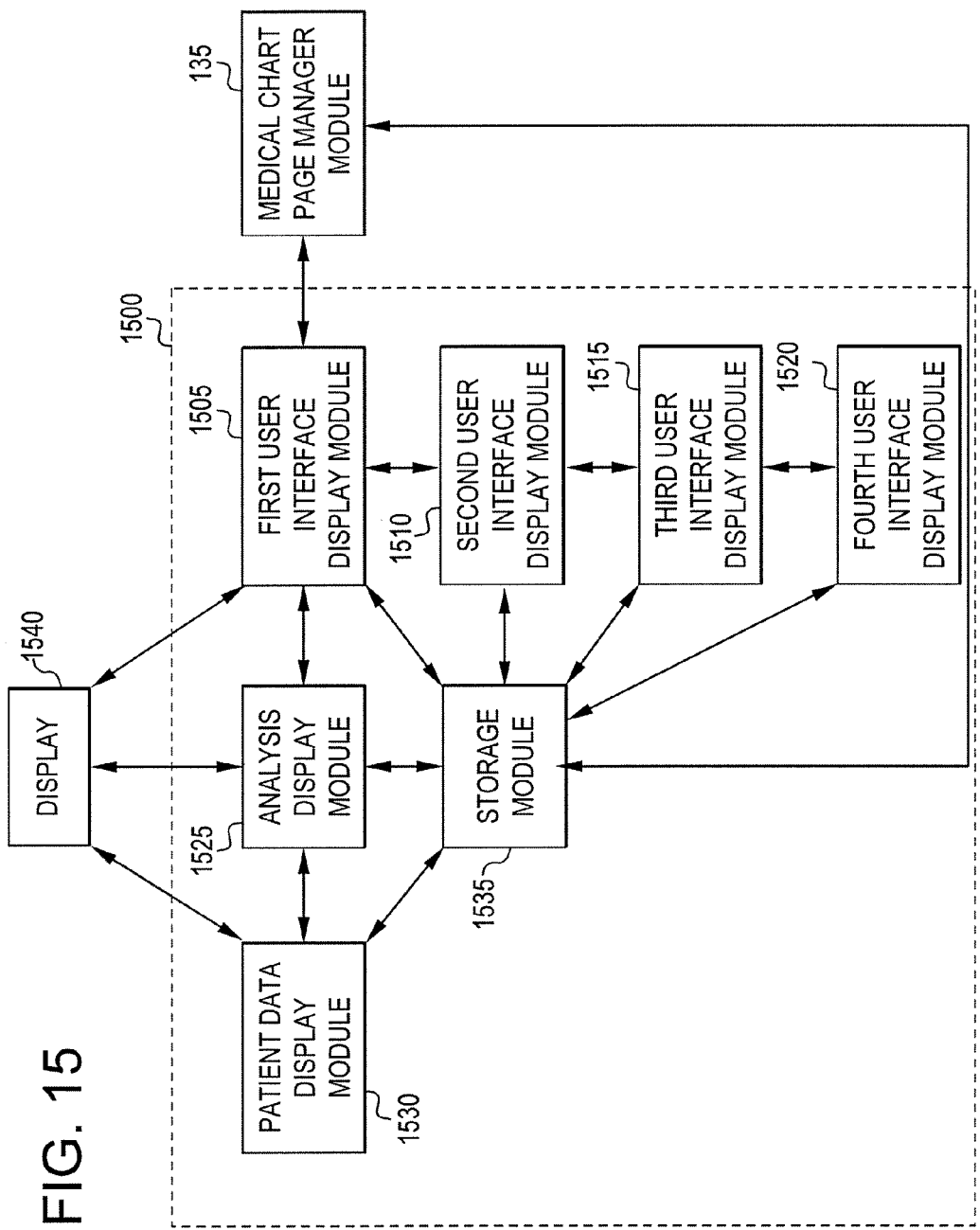
FIG. 15 is a diagram illustrating a system for sample analysis and medical data acquisition for patient management, in accordance with an alternative exemplary embodiment of the present invention.

Alternative architectures or structures can be used to implement the various functions of the system 100 as described herein. For example, functions from two or more modules can be implemented in a single module, or functions from one module can be distributed among several different modules. For purposes of illustration and not limitation, FIG. 15 is a diagram illustrating a system 1500 for sample analysis and medical data acquisition for patient management, in accordance with an alternative exemplary embodiment of the present invention. The system 1500 includes a first user interface display module 1505. The first user interface display module 1505 can be configured to display a medical chart page. The medical chart page can comprise at least one selectable item associated with patient management. One of the at least one selectable item can comprise, for example, a medical therapy delivery selection. The system 1500 includes a second user interface display module 1510 in communication with the first user interface display module 1505. The second user interface display module 1510 can be configured to display a list of medical therapy delivery systems associated with the medical therapy delivery selection from the medical chart page. A medical therapy delivery system can be chosen from the list of medical therapy delivery systems. The system 1500 includes a third user interface display module 1515 in communication with at least the first user interface display module 1505. The third user interface display module 1515 can be configured to display parameter fields for entry of operation data associated with the chosen medical therapy delivery system. Medical data captured from a patient by a medical analyzer can be analyzed in accordance with the operation data.

The system 1500 can include a fourth user interface display module 1520 in communication with at least the first user interface display module 1505. The fourth user interface display module 1520 can be configured to display a mode selection list associated with the chosen medical therapy delivery system. A mode can be chosen from the mode selection list. The third user interface display module 1515 can be configured to display the parameter fields in accordance with the chosen mode for entry of the operation data. The system 1500 can include an analysis display module 1525 in communication with at least the first user interface display module 1505. The analysis display module 1525 can be configured to display analysis results of the medical data analyzed in accordance with the operation data. The system 1500 can include a patient data display module 1530 in communication with at least the first user interface display module 1505. The patient data display module 1530 can be configured to display medical data associated with each patient. The system 1500 can include one or more storage modules 1535. The storage modules 1535 can be configured to store at least one of the operation data and the analyzed medical data for each patient. Any or all of the modules of the system 1500 can be in communication with the storage modules 1535. In addition, any or all of the modules of system 1500 can be configured to generate and display information via a display screen 1540. Other alternative architectures or structures can be used to implement the functions of the systems 100 and 1500 as described herein.

Figure 16:
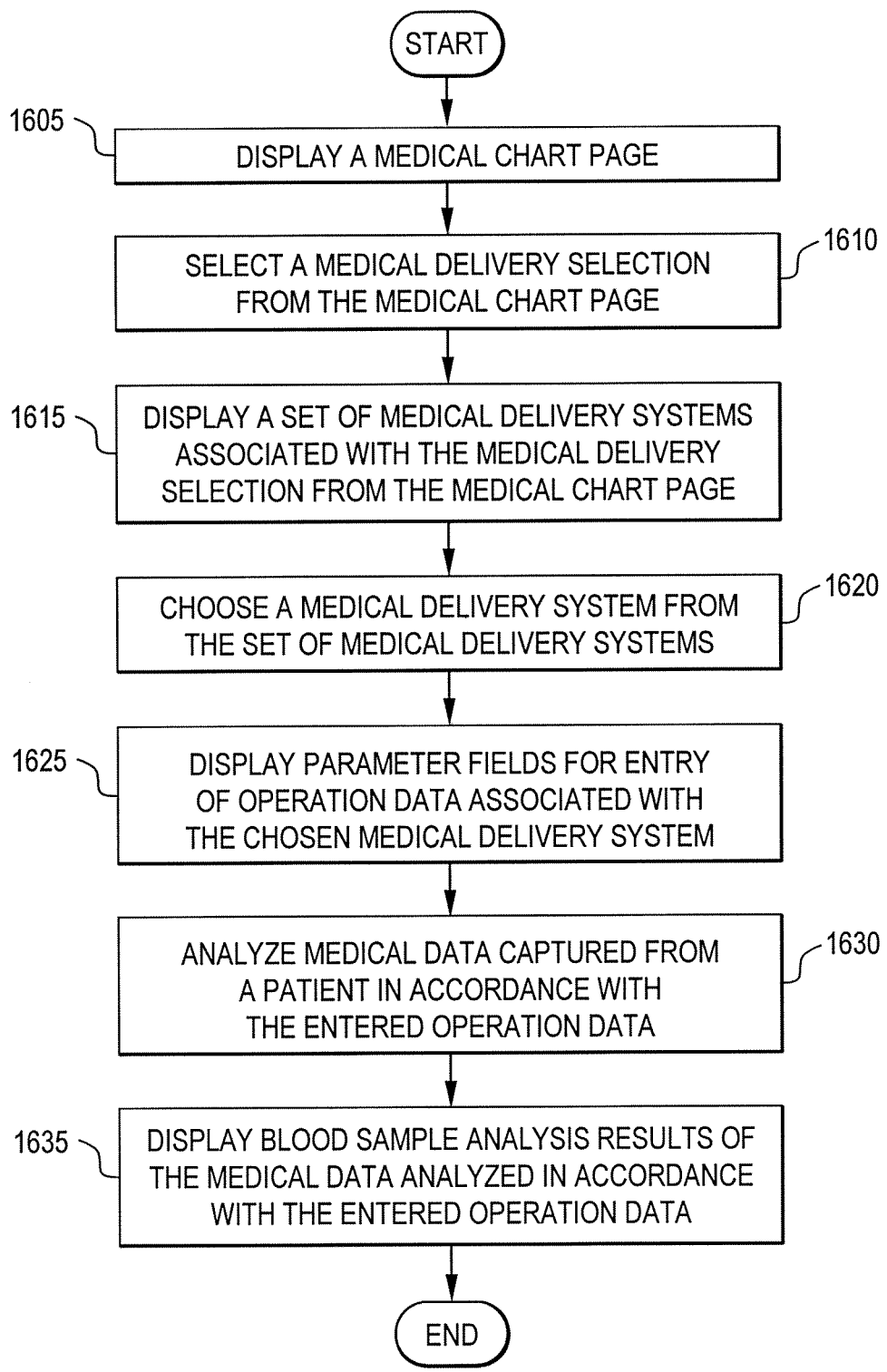
FIG. 16 is a flowchart illustrating steps for analyzing patient samples and acquiring medical data for managing patients, in accordance with an exemplary embodiment of the present invention.

FIG. 16 is a flowchart illustrating steps for analyzing samples and acquiring medical data for managing patients, in accordance with an exemplary embodiment of the present invention. In step 1605, a medical chart page can be displayed. The medical chart page can comprise at least one selectable item associated with patient management. One of the at least one selectable item can comprise a medical delivery selection. In step 1610, the medical delivery selection can be selected from the medical chart page. In step 1615, a set of medical delivery systems associated with the medical delivery selection from the medical chart page can be displayed. In step 1620, a medical delivery system can be chosen from the set of medical delivery systems. In step 1625, parameter fields for entry of operation data associated with the chosen medical delivery system can be displayed. In step 1630, medical data captured from a patient can be analyzed in accordance with the entered operation data. For example, step 1630 can be conducted by an analyzer configured to perform an analysis of a sample from the patient. In step 1635, sample analysis results of the medical data analyzed in accordance with the entered operation data can be displayed. For example, steps 1605, 1615, 1625 and 1635 can be configured to display information via the analyzer or other suitable display screen or device.

According to an exemplary embodiment, step 1635 can comprise the step of displaying the medical data along with the sample analysis results. Step 1620 can include the steps of displaying a mode selection list associated with the chosen medical delivery system, and choosing a mode from the mode selection list. Accordingly, step 1625 can include the step of displaying the parameter fields in accordance with the chosen mode for entry of the operation data. According to an exemplary embodiment, the method can include the step of displaying medical data associated with each patient. According to an alternative exemplary embodiment, medical chart pages are assigned to analyzer cartridge types, and the method can include the step of displaying the medical chart page assigned to an analyzer cartridge type being used. According to another alternative exemplary embodiment, medical chart pages can be assigned to operation data associated with each medical delivery system, and the method can include the step of displaying the medical chart page assigned to the operation data associated with the chosen medical delivery system. Alternatively, medical chart pages can be assigned to medical data associated with each patient, and the method can include the step of displaying the medical chart page assigned to the medical data associated with the patient. Additionally or alternatively, the method can include the step of displaying the chosen medical delivery system in the medical chart page. Furthermore, the method can include the step of storing the operation data and/or the sample analysis results for each patient.

Any or all of the steps of a computer program as illustrated in FIG. 16 for analyzing samples and acquiring medical data for managing patients can be embodied in any computer-readable medium for use by or in connection with an instruction execution system, apparatus, or device, such as a computer-based system, processor-containing system, or other system that can fetch the instructions from the instruction execution system, apparatus, or device and execute the instructions. As used herein, a "computer-readable medium" can be any means that can contain, store, communicate, propagate, or transport the program for use by or in connection with the instruction execution system, apparatus, or device. The computer readable medium can be, for example but not limited to, an electronic, magnetic, optical, electromagnetic, infrared, or semiconductor system, apparatus, device, or propagation medium. More specific examples (a non-exhaustive list) of the computer-readable medium can include the following: an electrical connection having one or more wires, a portable computer diskette, a random access memory (RAM), a read-only memory (ROM), an erasable programmable read-only memory (EPROM or Flash memory), an optical fiber, and a portable compact disc read-only memory (CDROM).

Exemplary embodiments of the present invention can be used in conjunction with any device, system or process for capturing, reading, analyzing, and/or delivering medical therapy to patients, particularly when how such device, system or process is set up can affect the interpretation of the analysis results. For example, exemplary embodiments can be used to analyze the patient's medical data in accordance with the operating parameters of the given device, system or process to provide a better interpretation of such medical data.

It will be appreciated by those of ordinary skill in the art that the present invention can be embodied in various specific forms without departing from the spirit or essential characteristics thereof. The presently disclosed embodiments are considered in all respects to be illustrative and not restrictive. The scope of the invention is indicated by the appended claims, rather than the foregoing description, and all changes that come within the meaning and range of equivalence thereof are intended to be embraced.

All United States patents and patent applications, foreign patents and patent applications, and publications discussed above are hereby incorporated by reference herein in their entireties to the same extent as if each individual patent, patent application, or publication was specifically and individually indicated to be incorporated by reference in its entirety.

What is claimed is:

1. A sample analysis and medical data acquisition system for patient management, comprising:

an analyzer cartridge of a specified type defined by one or more analytical tests that the analyzer cartridge is configured to perform; and an analyzer comprising:

an electromechanical port configured to mate with the analyzer cartridge;

a processor configured to execute program instructions to:

indentify the type of the analyzer cartridge upon the electromechanical port mating with the analyzer cartridge;

generate and transmit a signal indicative of the identified type of the analyzer cartridge;

perform the one or more analytical tests on a sample obtained from a patient that is dispensed within the analyzer cartridge; and obtain medical data from the performance of the one or more analytical tests;

a first user interface display module comprised of any combination of hardware, firm ware, and software that is configured to:

receive the signal indicative of the identified type of the analyzer cartridge;

obtain a medical chart page from a computer storage memory using the received signal, wherein the medical chart page is associated with the identified type of the analyzer cartridge;

display the medical chart page, wherein the displayed medical chart page comprises at least one selectable item comprising one or more medical therapy delivery systems associated with management of the patient; and receive and transmit a selection of at least one of the one or more medical therapy delivery systems;

a second user interface display module comprised of any combination of hardware, firm ware, and software that is configured to:

receive the selection of the at least one of the one or more medical therapy delivery systems;

display parameter fields for entry of operation data associated with the selected at least one of the one or more medical therapy delivery systems; and receive the operation data associated with the selected at least one of the one or more medical therapy delivery systems; and an analysis display module comprised of any combination of hardware, firm ware, and software that is configured to display sample analysis results of the medical data that is analyzed in accordance with the received operation data associated with the selected at least one of the one or more medical therapy delivery systems, wherein the processor is further configured to execute the program instructions to analyze the medical data obtained from the performance of the one or more analytical tests in accordance with the received operation data that is dependent upon the identified type of the analyzer cartridge.

2. The system of claim 1, wherein the sample is one of blood, serum, plasma, urine, saliva, cheek swab and cerebrospinal fluid.

3. The system of claim 1, wherein the analysis display module is further configured to display the medical data along with the sample analysis results.

4. The system of claim 1, further comprising a third user interface display module in communication with at least the first user interface display module, wherein the third user interface display module is configured to display a mode selection list associated with the selected at least one of the one or more medical therapy delivery systems, wherein a mode is chosen from the mode selection list, and wherein the second user interface display module is further configured to display the parameter fields in accordance with the chosen mode for entry of the operation data.

5. The system of claim 1, further comprising a patient data display module in communication with at least the first user interface display module, wherein the patient data display module is configured to display medical data associated with each patient.

6. The system of claim 1, wherein the first user interface display module is further configured to obtain and display a plurality of medical chart pages using the received signal, wherein each of the plurality of medical chart pages is associated with the identified type of the analyzer cartridge, and wherein the first user interface display module is further configured to display each of the plurality of medical chart pages in accordance with the identified type of the analyzer cartridge being used with the analyzer.

7. The system of claim 6, further comprising a medical chart page manager module in communication with at least the first user interface display module.

8. The system of claim 7, wherein the medical chart page manager module is configured to assign each of the plurality of medical chart pages to the identified type of the analyzer cartridge.

9. The system of claim 7, wherein the medical chart page manager module is configured to assign each of the plurality of medical chart pages to operation data associated with each of the one or more medical therapy delivery systems.

10. The system of claim 7, wherein the medical chart page manager module is configured to assign each of the plurality of medical chart pages to medical data associated with each patient.

11. The system of claim 1, wherein the medical chart page further comprises at least one parameter field for entry of medical data associated with the patient.

12. The system of claim 1, wherein the medical chart page is configured to display the selected at least one of the one or more medical therapy delivery systems.

13. The system of claim 1, wherein the medical chart page is customizable in accordance with a location of use of the sample analysis and medical data acquisition system.

14. The system of claim 13, wherein the location comprises a location within a hospital.

15. The system of claim 14, wherein the location within the hospital is one of an intensive care unit, a critical care unit, a general ward, an operating room and an emergency department.

16. The system of claim 1, wherein the medical chart page is customizable in accordance with the analyzer cartridge.

17. The system of claim 16, wherein the analyzer cartridge comprises a disposable biological fluid analysis cartridge.

18. The system of claim 1, wherein the first and second user interface display modules and the analysis display module are further configured to display information via the analyzer.

19. The system of claim 1, wherein the first and second user interface display modules and the analysis display module are further configured to display information via a display screen.

20. The system of claim 1, wherein the analyzer comprises a portable point-of-care biological fluid analysis device.

21. The system of claim 1, wherein the sample analysis and medical data acquisition system is in communication with the analyzer.

22. The system of claim 1, further comprising a storage module in communication with at least the first user interface display module, wherein the storage module is configured to store at least one of the operation data and the sample analysis results for each patient.

23. The system of claim 1, wherein the selected at least one of the one or more medical therapy delivery systems comprises a respiratory delivery system.

24. The system of claim 23, wherein the respiratory delivery system comprises a ventilator.

25. The system of claim 24, wherein the operation data comprises ventilator machine settings.

26. The system of claim 1, wherein the one or more analytical tests are electrochemical or optical analytical tests.

\* \* \* \* \*